United States Patent
Berezin et al.

(10) Patent No.: US 9,044,428 B2
(45) Date of Patent: *Jun. 2, 2015

(54) NEURITOGENIC PEPTIDES

(71) Applicant: Neoloch ApS, Charlottenlund (DK)

(72) Inventors: Vladimir Berezin, Copenhagen (DK); Elisabeth Bock, Charlottenlund (DK)

(73) Assignee: Neoloch ApS, Charlottenlund (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,715

(22) Filed: Nov. 19, 2012

(65) Prior Publication Data

US 2013/0123174 A1    May 16, 2013

Related U.S. Application Data

(63) Continuation of application No. 11/913,954, filed as application No. PCT/DK2006/000246 on May 8, 2006, now Pat. No. 8,329,652.

(30) Foreign Application Priority Data

May 10, 2005    (DK) .................................. 2005 00671

(51) Int. Cl.
| | |
|---|---|
| A01N 37/18 | (2006.01) |
| A61K 38/00 | (2006.01) |
| A61K 38/10 | (2006.01) |
| C07K 14/505 | (2006.01) |
| A61K 38/08 | (2006.01) |

(52) U.S. Cl.
CPC ............... *A61K 38/10* (2013.01); *C07K 14/505* (2013.01); *A61K 38/08* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 4,599,311 A | 7/1986 | Kawasaki | |
| 4,683,202 A | 7/1987 | Mullis | |
| 4,703,008 A | 10/1987 | Lin | |
| 4,816,567 A | 3/1989 | Cabilly et al. | |
| 4,946,778 A | 8/1990 | Ladner et al. | |
| 5,106,954 A | 4/1992 | Fibi et al. | |
| 5,614,184 A | 3/1997 | Sytkowski et al. | |
| 5,700,909 A | 12/1997 | O'Brien | |
| 6,153,407 A | 11/2000 | Sytkowski et al. | |
| 6,340,742 B1 | 1/2002 | Burg et al. | |
| 6,642,363 B1 | 11/2003 | Mooney et al. | |
| 6,703,480 B1 | 3/2004 | Balu | |
| 8,329,652 B2 * | 12/2012 | Berezin et al. ............... 514/17.7 |
| 2003/0130197 A1 | 7/2003 | Smith-Swintosky et al. | |
| 2003/0191291 A1 | 10/2003 | Kochendoerfer et al. | |
| 2006/0135754 A1 | 6/2006 | Christensen et al. | |

FOREIGN PATENT DOCUMENTS

| | | |
|---|---|---|
| EP | 0 238 023 | 12/1993 |
| EP | 404 097 | 9/1996 |
| WO | WO 93/11161 | 6/1993 |
| WO | WO 00/18791 | 4/2000 |
| WO | WO 2004/018515 | 3/2004 |

OTHER PUBLICATIONS

Tabria et al., Neurotrophic effect of hematopoietic cytokines on cholinergic and other neurons in vitro. Int J Dev Neurosci (1995) 13(3/4) 241-252.
Vasuvedan et al., Muscarinic acetylcholine receptor produced in recombinant baculovirus infected Sf9 insect cells couples with endogenous G-proteins to activate ion channels. 1992, FEBS Lett. 311:7-11.
Vaswani, et al., Humanized antibodies as potential therapeutic drugs. 1998, Annals Allergy, Asthma & Immunol 81:105-115.
Wen et al., Erythropoietin structure-function relationships. J Biol Chem (1994) 269(36):22839-22846.
Whitlow et al., Single-chain Fv proteins and their fusion proteins. 1991, In: Methods: A Companion to Methods in Enzymology, 2:97.
Wigler et al., Biochemical transfer of single-copy eucaryotic genes using total cellular DNA as donor. 1978, Cell 14:725.
Winearls C. G. et al. Effect of human erythropoietin derived from recombinant DNA on the anaemia of patients maintained by chronic haemodialysis. The Lancet (1986) 2 (8517) 1175-1177.
Wrighton, N.C. et al., Small Peptides as Potent Mimetics of the Protein Hormone Erythropoietin. Science, vol. 273, Jul. 26, 1996, pp. 458-463.
Young et al., The Alcohol dehydrogenase genes of the yeast, saccharomyces cerevisiae: Isolation, structure and regulation. 1982, in Genetic Engineering of Microorganisms for Chemicals, editors A Hollaender and RD Demoss 335-361.
Siren et al., 2001 PNAS, vol. 98, 7, pp. 4044-4049.
Campana et al., 1995, J. Neurochem., vol. 64, Suppl. 1, pp. S24.
Smith-Swintosky et al., 2001, Soc. for Neuroscience Abstracts, vol. 27, No. 1, pp. 929.
Johnson et al., "Identification of a 13 Amino Acid Peptide Mimetic of Erythropoietin and Description of Amino Acids Critical for the Mimetic Activity of EMP1" Biochemistry, vol. 37, pp. 3699-3710, 1998.
Livnah et al., "An antagonist peptide-EPO receptor complex suggests that receptor dimerization is not sufficient for activation" Nature Structural Biology, vol. 5, No. 11, pp. 993-1004, Nov. 1998.

(Continued)

*Primary Examiner* — Olga N Chernyshev
(74) *Attorney, Agent, or Firm* — Posternak Blankstein & Lund LLP

(57) ABSTRACT

The present invention relates to peptide compounds that are capable of stimulating neuronal differentiation, neurite outgrowth and survival of neural cells, and enhancing synaptic plasticity, learning and memory, methods of treating diseases and conditions of nervous system by administration of compositions comprising said compounds. The compounds and compositions of the invention include peptide sequences that are derived from the sequence of human erythropoietin or proteins that are homologous of human erythropoietin.

10 Claims, 16 Drawing Sheets

(56) References Cited

OTHER PUBLICATIONS

Figure 1:
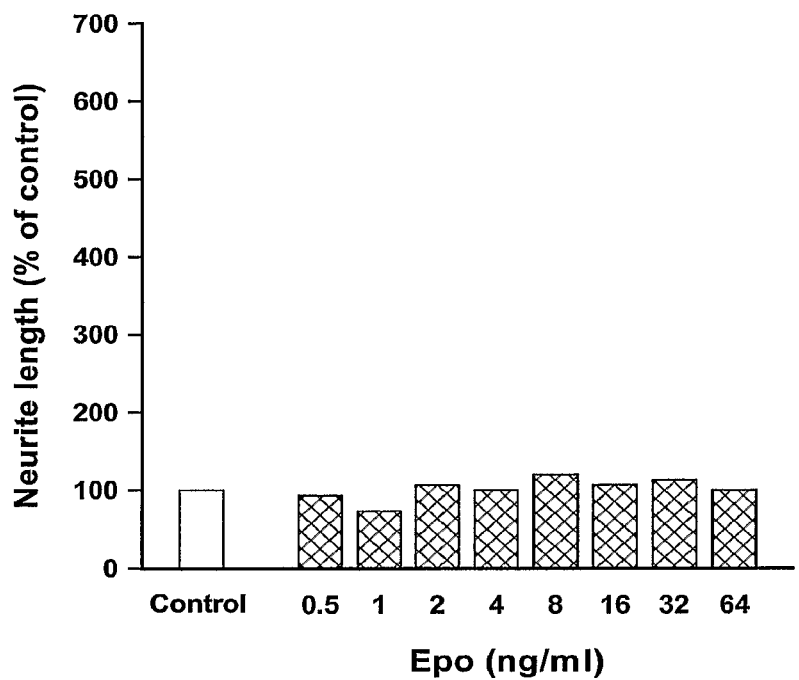

Nagao et al., "In vivo neuroprotective activity of Epopeptide AB against ischemic damage" Cytotechnology, vol. 47, pp. 139-144, 2005.

Pankratova et al., "Neuroprotective properties of a novel, non-haematopoietic agonist of the erythropoietin receptor" Brain, downloaded from http://brain.oxfordjournals.org at New Copenhagen University on May 6, 2010, pp. 1-14.

Corsara and Pearson, Enhancing the efficiency of DNA-medicated gene transfer in mammalian cells, 1981, in Somatic Cell Genetics, 7. p. 603.

Dame, C. et al., The Biology of Erythopoietin in the Central Nervous System and its Neurotrophic and Neuroprotective Potential, Biol Neonate, 2001, 79:228-235.

Hollaender et al., eds., Trends in the biology of fermentations for fuels and chemicals, Plenum Press, 1981, pp. 242-272.

Coligan et al., Production of Polyclonal Antisera in Rabbits, Rats, Mice and Hamsters, Current Protocols in Immunology, 1995, sections 2.4.1, 2.5.1-2.6.7.

Alber and Kawasaki Nucleotide sequence of the triose phosphate isomerase gene of *Saccharomyces cerevisiae*, 1982, J. Mol. Appl. Gen. 1: 419-434.

Baines, et al. Purification of Immunoglobulin G (IgG). In: Methods in Molecular Biology, 1992, 10:79-104, Humana Press, NY.

Beaucage and Caruthers, Deoxynucleoside phosphoramidities-a new class of key intermediates for deoxpolynucleotide synthesos, 1981, Tetrahedron Lett. 22:1859-1869.

Beckman, B S, Mason-Garcia M. Signal transduction in erythropoiesis. The Faseb Journal (1991) 5: 2958-2964.

Bird et al., Single chain antigen-binding proteins, 1988, Science, 242:423-426.

Campana et al., Identification of a neurotrophic sequence in erythropoietin, International Journal of Molecular Medicine 1: 235-241, 1998.

Cheetham et al., NMR structure of human erythropoietin and a comparison with its reception bound confirmation, Nat Str Biol (1998) 5(10):861-866.

Clackson et al., Making antibody fragments using phage display libraries, 1991, Nature 352: 624-628.

Dryland, A. and Sheppard, R.C., Peptide synthesis. Part 8. A system for solid-phase synthesis under low pressure continuous flow conditions (1986) J. Chem. Soc. Perkin Trans. 1, 125-137.

Elliott et al., Mapping of the active site of recombinant human erythropoietin, Blood (1997) 89(2):493-502.

Eschbach J.W. et al., Correction of the anemia of end-stage renal disease with recombinant human erythropoietin. New Eng J Med (1987) 316:73-78.

Graham and van der Eb, A new technique for the assay of infectivity of human adenovirus 5 DNA, 1973, Virol, 52:456, pp. 456-467.

Grant, G.A., Synthetic Peptides: A User's Guide (Advances in Molecular Biology) Ed, Oxford University Press, 2002, pp. 8-9, 81-92, 173-219, 285-291, 358-376.

Green et al., 1992, Production of Polyclononal Antisera in Immunochemical Protocols (Manson, ed.) pp. 1-5 (Humana Press).

Grodberg et al., Alanine scanning mutagenesis of human erythropoietin identifies four aminio acids which are critical for biological activity, Eur J. Biochem (1993) 218(2):597-601.

Harlow and Lane, Antibodies: A Laboratory Manual, Cold Spring Harbor Laboratory, NY, 1988, pp. 697-726.

Hitzeman et al., Isolation and characterization of the yeast 3-phosphoglycerokinase gene (PGK) by an immunological screening technique, 1980, J. Biol. Chem. 255:12073-12080.

Hollinger et al., Diabodies: Small bivalent and specific antibody fragments. Proc. Natl. Acad. Sci. USA 90:6444-6448 (1993).

Holmes et al., Structural consequences of humanizing an antibody. 1997, J Immunol 158:2192-2201.

IUPAC-IUB Joint Commission on Biochemical Nomenclature (JCBN). Nomenclature and symbolism for amino acids and peptides. Pure & Appl. Chem. vol. (56(5) pp. 595-624 (1984).

Jones et al., Replacing the complmentarity-determining regions in a human antibody with those from a mouse. 1986, Nature 321, 522-525.

Juul et al., Erythropoietin and erythropoietin receptor in the developing human central nervous system. Pediatr Res (1998) 43(1) 40-49.

Juul et al., Erythropoietin in the cerebrospinal fluid of neonates who sustained CNS injury. Ped Res (1999) 46(5) 543-547.

Juul et al., Immunohistochemical localization of erythropoietin and its receptor in the developing human brain. Pediatr Dev Pathol (1999) 2(2) 148-158.

Kaufman and Sharp, Amplification and expression of sequences cotransfected with a modular dihydrofolate reductase complementary DNA gene. J. Mol. Biol. 159, 1982, pp. 601-621.

Kohler & Milstein, Continuous cultures of fused cells secreting antibody of predefined specificity. Nature, 256: 495-7 (1975).

Koshimura et al., Effects of erythropoietin on neuronal activity. J. Neurochem (1999)72(6) 2565-2572.

Krantz S. B., Erythropoietin. Blood (1991) 77:419-434.

Larrick et al., PCR Amplification of antibody genes. Methods, a Companion to Methods in Enzymology, vol. 2, p. 106 (1991).

Loyter et al., Mechanisms of DNA uptake by mammalian cells: Fate of exogenously added DNA monitored by the use of fluorescent dyes. 1982, Proc. Natl. Acad. Sci. USA 79:422-426.

Marks et al., By-passing immunization human antibodies from V-gene libraries displayed og phage. 1991. J Mol Biol 222: 581-597.

Matthes et al., Simultaneous rapid chemical synthesis of over one hundred oligonucleotides on a microscale. 1984 EMBO J. 3.801-805.

McKnight et al., Identification and molecular analysis of a third aspergillus nidulans alcohol dehydrogenase gene. 1985, EMBO J. 4:2093-2099.

Morishita et al., Erythropoietin receptor is expressed in rat hippocampal and cerebral cortical neurons, and erythropoietin prevents in vitro glutamate-induced neuronal death. Neuroscience (1997) 76(1) 105-116).

Morrison et al., Chimeric human antibody molecules: Mouse antigen-binding domains with human constant region domains. 1984, Proc Nati Acad Sci USA, 81:6851-6855.

Neumann et al., Gene transfer into mouse lyoma cells by electroporation in high electric fields. 1982, EMBO J. 1:841-845.

Novotny J. & Haber E., Structural invariants of antigen binding. Comparison of immunoglobin VL-VH and VL-VL domain dimers. Proc Natl Acad Sci USA 82(14):4592-6, 1985.

Pack et al., Improved bivalent miniantibodies with identical avidity as whole antibodies, produced by high cell density fermentation of *Escherichia coli*. 1993, BioTechnology 11:1271-77.

Palmiter et al., Metallothionein-human GH fusion genes stimulate growth of mice,1983 Science 222:809-814.

Pluckthun, A., Antibodies from *Escherichia coli*. Pharmacology of Monoclonal Antibodies 113:269-315, Rosenburg and Moore eds., Springer-Verlag NY, 1994.

Presta, L.G., Antibody engineering. 1992, Curr Op Struct Biol 2:593-596.

Reichmann et al., Reshaping human antibodies for therapy. 1988, Nature 332, 323-329.

Russell et al., DNA sequences of two yeast promoter-up mutants. 1983, Nature 304:652-654.

Sadamoto et al., Erythropoietin prevents place navigation disability and cortical infarction in rates with permanent occlusion of the middle cerebral artery. Biochem Biophys Res Commun (1998) 253(1) 26-32.

Saiki et al., Primer-directed enzymatic amplification of DNA with a thermostable DNA polymerase. 1988. Science 239:487-491.

Sakanaka et al., In vivo evidence that erythropoietin protects neurons from ischemic damage. Proc Natl Acad Sci USA (1998) 95(8) 4635-4640.

Schousboe, A. et al., Evidence for evoked release of adenosine and glutamate from cultured cerebellar granule cells. Neurochemical Research, vol. 14, No. 9, 1989, pp. 871-875.

(56) References Cited

OTHER PUBLICATIONS

Southern and Berg, Transformation of Mammalian cells to antibiotic resistance with a bacterial gene under control of the SV40 early region promoter. 1982, J. Mol. Appl. Genet. 1:327-341.

Subramani et al., Expression of the mouse dihydrofolate reductase complementary deoxyribonucleic acid in simian virus 40 vectors. 1981, Mol. Cell Biol. 1:854-864.

Syed et al., Efficiency of signaling through cytokine receptors depends critically on receptor orientation. Nature (1998) 395:516.

* cited by examiner

* and *** indicate p<0.05 and p<0.001, respectively, compared with control

*,  and * indicate p<0.05, p<0.01 and p<0.001, respectively, compared with control and * indicate p<0.01 and p<0.001, respectively, compared with control

* and *** indicate p<0.05 and p<0.001, respectively, compared with control

*,  and * indicate p<0.05, p<0.01 and p<0.001, respectively, compared with control.

NEURITOGENIC PEPTIDES

FIELD OF THE INVENTION

The present invention relates to compounds that are capable of stimulating neuronal differentiation, neurite outgrowth and survival of neural cells, and enhancing synaptic plasticity, learning and memory, methods of treating diseases and conditions of nervous system by administration of compositions comprising said compounds. The compounds and compositions of the invention include peptides and/or peptide multimers that derived from human erythropoietin or proteins that are homologous of human erythropoietin.

BACKGROUND OF THE INVENTION

Erythropoietin (EPO) is a glycoprotein hormone produced by the kidney in response to tissue hypoxia that stimulates red blood cell production in the bone marrow. The gene for erythropoietin has been cloned and expressed in Chinese hamster ovary (CHO) cells as described in U.S. Pat. No. 4,703,008. Recombinant human erythropoietin (r-HuEPO or Epoetin alfa) has an amino acid sequence identical to that of human urinary erythropoietin, and the two are indistinguishable in chemical, physical and immunological tests. Recombinant human erythropoietin acts by increasing the number of cells capable of differentiating into mature erythrocytes, triggering their differentiation and augmenting hemoglobin synthesis in developing erythroblasts (Krantz S B. Blood (1991) 77: 419-434, Beckman B S, Mason-Garcia M. The Faseb Journal (1991) 5: 2958-2964).

Epoetin alfa has been well tolerated in studies conducted to date. Hypertensive encephalopathy and seizures have occasionally been described in dialysis patients treated with Epoetin alfa, particularly during the early phase of therapy when hematocrit is rising. (Eschbach J W, Egrie J C, Downing M R, Browne J K. Adamson J W. New Engl J Med (1987) 316: 73-78, Winearls C G. Oliver D O, Pippard M J, et al. Lancet (1986) 2 (8517): 1175-1177). Such reports became more rare as experience of use of the compound developed. Occasionally, cancer patients treated with Epoetin alfa have experienced an increase in blood pressure associated with a significant increase in hematocrit. The risk, however, appears substantially lower than in chronic renal failure patients.

No antibody titers against Epoetin alfa could be demonstrated and confirmed in subjects treated with Epoetin alfa for up to 2 years, indicating the absence of immunological sensitivity to Epoetin alfa. Skin rashes and urticaria have been observed rarely and when reported have been mild and transient in nature, but these events suggest allergic hypersensitivity to some components of the Epoetin alfa formulation.

Epoetin an is approved for sale in many countries for the treatment of anemia in chronic renal failure (dialysis and predialysis), anemia in zidovudine treated HIV positive patients (US), anemia in cancer patients receiving platinum-based chemotherapy, as a facilitator of autologous blood pre-donation, and as a peri-surgical adjuvant to reduce the likelihood of requiring allogeneic blood transfusions in patients undergoing orthopedic surgery.

EPO influences neuronal stem coils, likely during embryonic development, and possibly during in vitro experiments of differentiation. (Juul et al Pediatr Dev Pathol (1999) 2(2) 148-158. Juul et al Pediatr Res (1998) 43(1) 40-49.) Further, neonates and infants that suffer CNS injury via hypoxia, meningitis, and intraventricular hemorrhage, show an EPO induced neuroprotective effect (Juul et al Pod Res (1999) 46(5) 543-547.)

EPO helps prevent apoptosis of neural tissue in cases of injury that create hypoxia. This may be the result of EPO produced locally by astrocytes (Morishita et al Neuroscience (1996) 76(1) 105-116). Neuroprotection has been demonstrated in gerbil hippocampal and rat cerebrocortical tissue (Sakanaka et al PNAS (1998) 95(8) 4635-4640. Sadamoto et al Biochem Biophys Res Commun (1998) 253(1) 26-32).

EPO induces biological effects of PC12 cells, including changes in Ca<2+>, changes in membrane potential, and promotion of neuronal survival. This has been interpreted that EPO can stimulate neural function and viability (Koshimura et al J. Neurochem (1999) 72(6) 2565-2572. Tabria et al Int J Dev Neurosci (1995) 13(3/4) 241-252.).

A number of studies were attempted to associated diverse biological activities of EPO with the particular structural areas of the protein (Grodberg et al, Eur J Biochem (1993) 218(2):597-601; Wen et al. J Biol Chem (1994) 269(38): 22839-22846; Elliott et al. Blood (1997) 89(2):493-602; Cheetham et al. Nat Str Biol (1998) 5(10):861-866; Syed et al. Nature (1998) 395:516) Campana et al proposed that a 17 amino acid peptide sequence of EPO can act through the EPO-R (Erythropoietin receptor) to induce biological activity in NS20Y. SK-N-MC, and PC12 cells, which includes sprouting, differentiation and neuroprotection. Curiously this peptide does not promote proliferation of hematologic cells, thus it appears inactive in cell lines well understood for their sensitivity to EPO activity (Campana et al Int J Mol Med (1998) 1(1) 235-241).

Short peptide fragments of Epo or other peptide sequences that have the full range of biological activity of human erythropoietin or only certain biological activities of erythropoietin are of great interest as drug candidates and a number of patent applications has already described or contemplated the uses of such biologically active peptide fragments as neurotrofic or neuroprotective drugs (U.S. Pat. Nos. 5,700,909, 6,703,480, 6,642,363, 5,106,954, US2003130197). The present application provides new peptide fragments derived from Epo or Epo functional homologues that may be advantageously used in therapeutic treatment of diseases or conditions of neural system.

SUMMARY OF INVENTION

The present invention identifies a new group of peptide sequences which are potent stimulators of neurite outgrowth. Surprisingly, the sequences are also capable to protect neuronal cells from death and promote survival of said cells, and moreover, are capable of stimulating cell proliferation. The inventors identified the structural motif that present in all disclosed herein peptide sequences and correlated the presence of this motif with biological activity of the sequences.

Accordingly, in the first aspect the invention relates to a compound comprising at least one isolated peptide sequence of 6 to 25 amino acid residues comprising the amino acid sequence motif of the formula $$x^1-x^2-x^3-x^4-x^5-x^6,$$ (SEQ ID NO: 43)

wherein
$x^1$ is a charged amino acid residue,
$x^6$ is a hydrophobic amino acid residue or A, and
$x^2$, $x^3$, $x^4$ and $x^5$ is any amino acid residue The invention discloses a group of particular sequences comprising the above motif, wherein said sequences are either short peptide fragments of human erythropoietin or short fragments of proteins having a structural homology to human erythropoietin. The disclosed sequences possess neuritogenic activity, neuronal cell survival promoting activity, synaptic plasticity stimulating activity, and/or learning and memory stimulating activity and cell proliferation stimulating activity.

In another aspect the invention relates to use of a peptide sequence comprising the structural motif of above and/or a compound comprising such sequence for the stimulating neurite outgrowth and/or promoting survival of neural cells, the manufacture of a medicament for treatment of conditions of the central and peripheral nervous system, the manufacture of a medicament for the stimulation of the ability to learn and/or the short and/or long-term memory the production of an antibody capable of recognizing an epitope comprising the sequence;

the treatment an individual in need.

The invention also related to a pharmaceutical composition comprising a compound and/or peptide sequence of the invention.

In further aspect the invention relates to an antibody capable of recognizing the epitope comprising a sequence comprising the motif of the invention.

FIGURE LEGENDS

Figure 2:
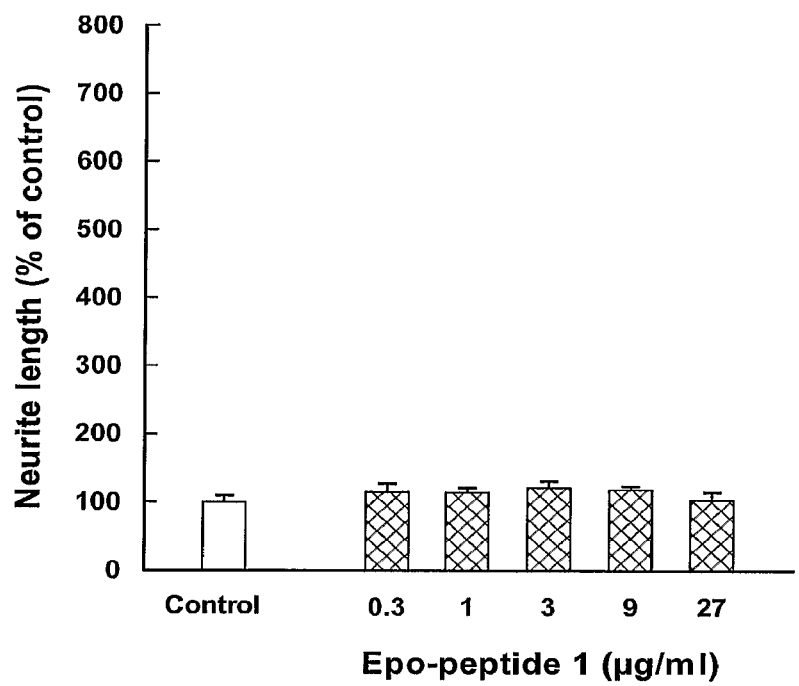
Figure 3:
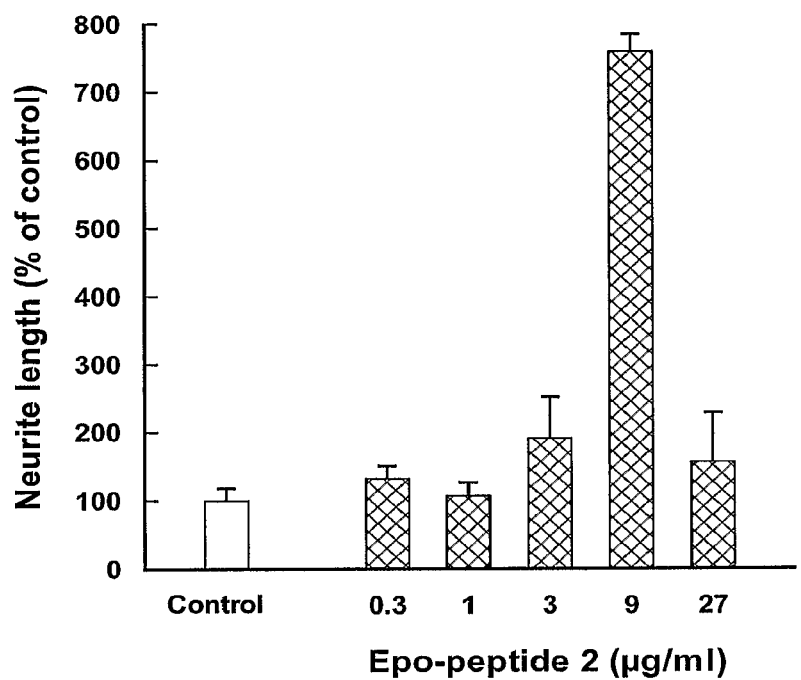

FIG. 1 Effect of recombinant human erythropoietin (Epo) on neurite outgrowth from CGN FIG. 2 Effect of Epo1 (Epo-peptide 1) (SEQ ID NO: 1) on neurite outgrowth from CGN FIG. 3 Effect of Epo2 (Epo-peptide 2) (SEQ ID NO: 2) on neurite outgrowth from CGN in vitro.

Figure 4:
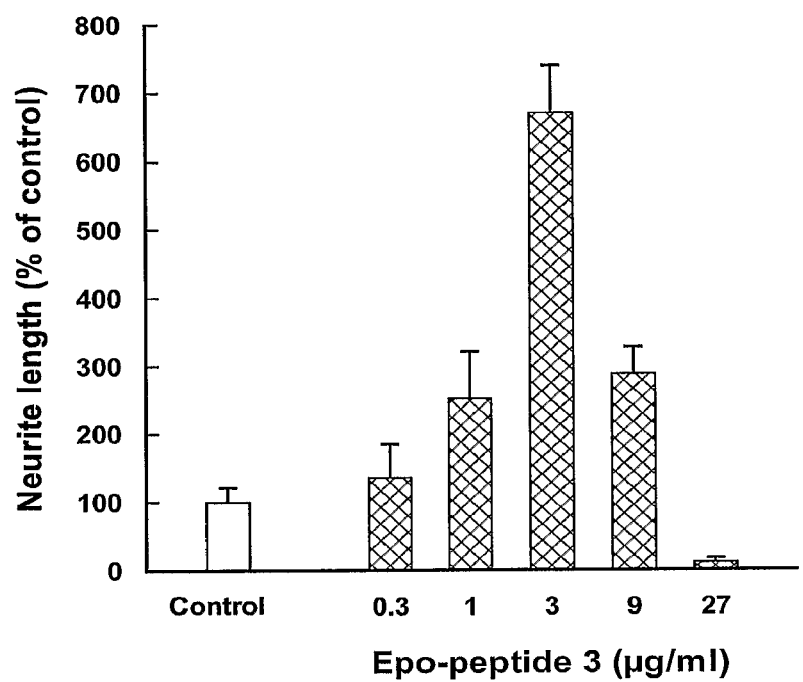

FIG. 4 Effect of Epo3 (Epo-peptide 3) (SEQ ID NO: 3) on neurite outgrowth from CGN in vitro.

Figure 5:
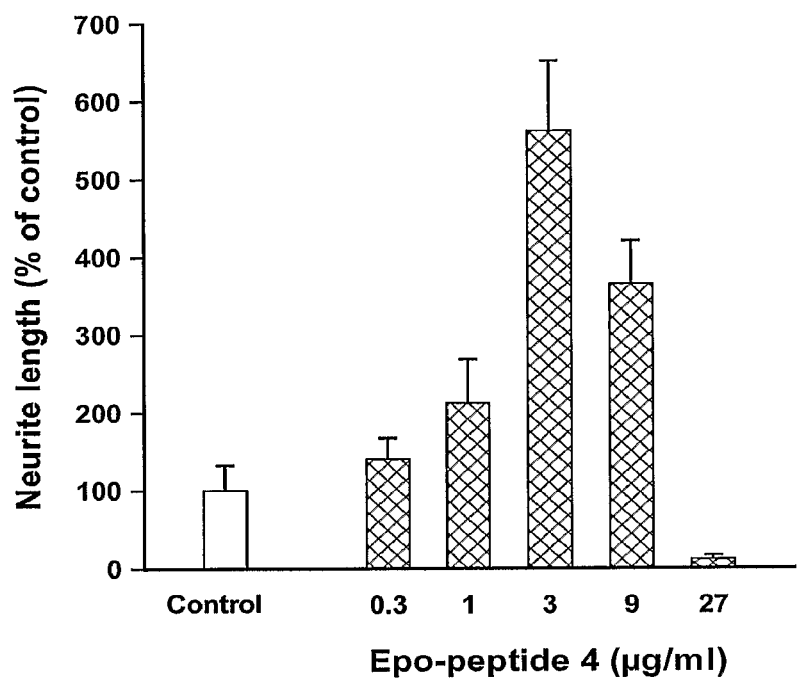

FIG. 5 Effect of Epo4 (Epo-peptide 4) (SEQ ID NO; 4) on neurite outgrowth from CGN in vitro.

Figure 6:
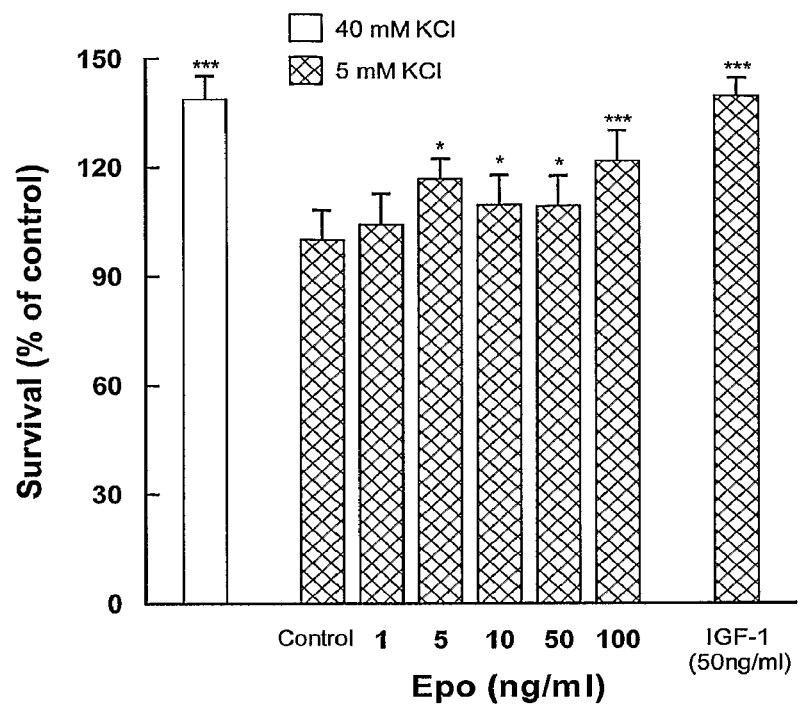

FIG. 6 Effect of recombinant human erythropoietin (Epo) on survival of CGN in vitro.

Figure 7:
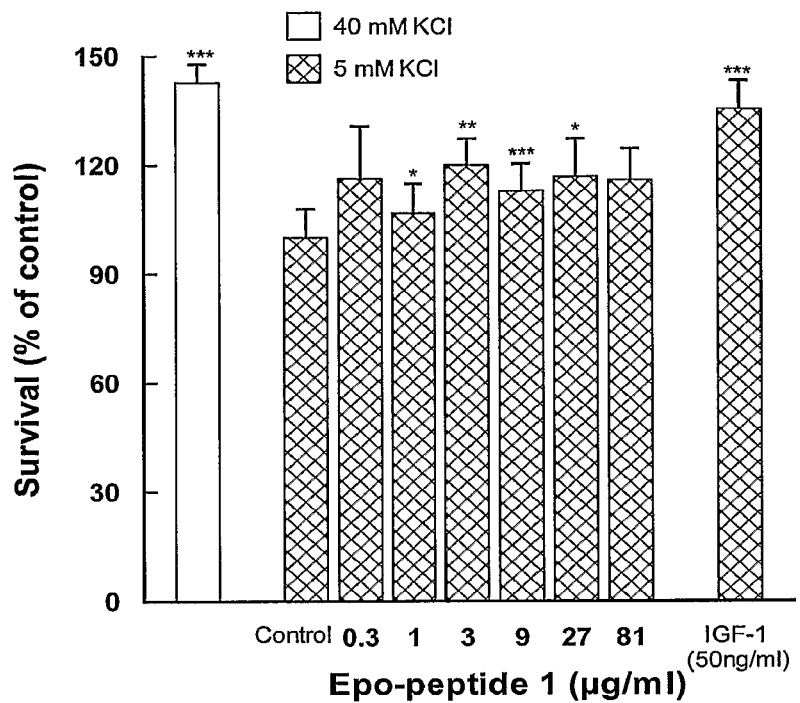

FIG. 7 Effect of Epo1 (Epo-peptide 1) (SEQ ID NO: 1) on survival of CGN in vitro.

Figure 8:
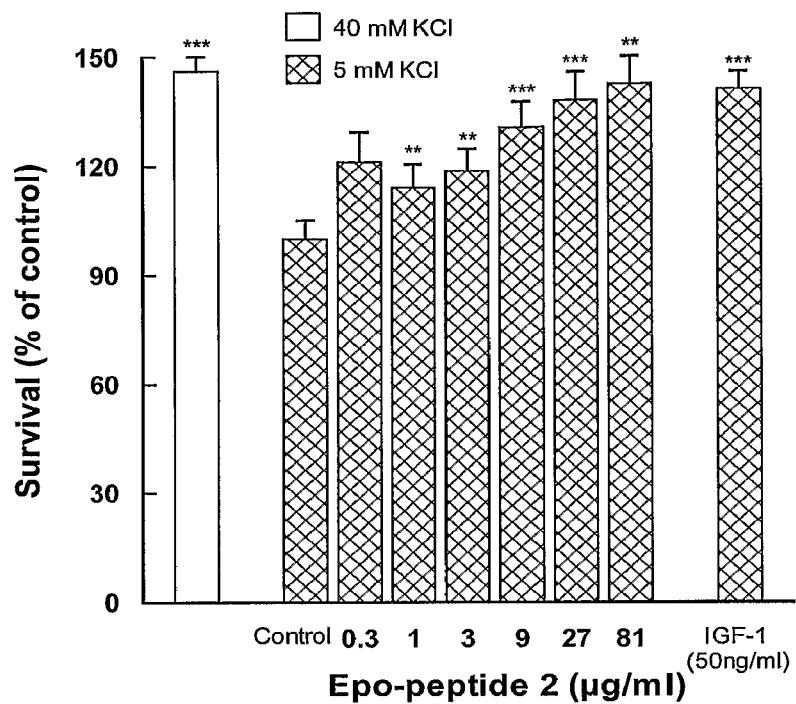

FIG. 8 Effect of Epo2 (Epo-peptide 2) (SEQ ID NO; 2) on survival of CGN in vitro.

Figure 9:
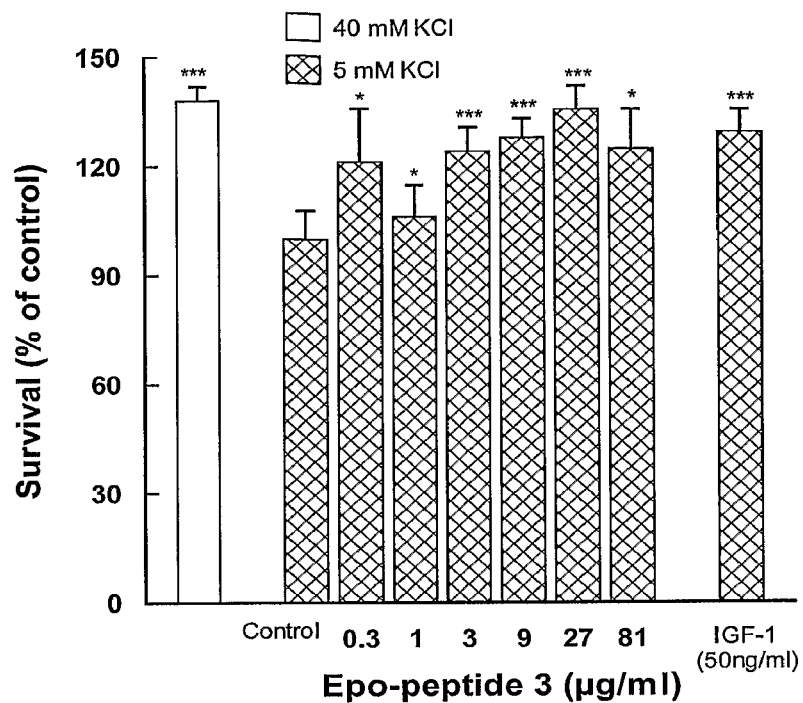

FIG. 9 Effect of Epo3 (Epo-peptide 3) (SEQ ID NO: 3) on survival of CGN in vitro.

Figure 10:
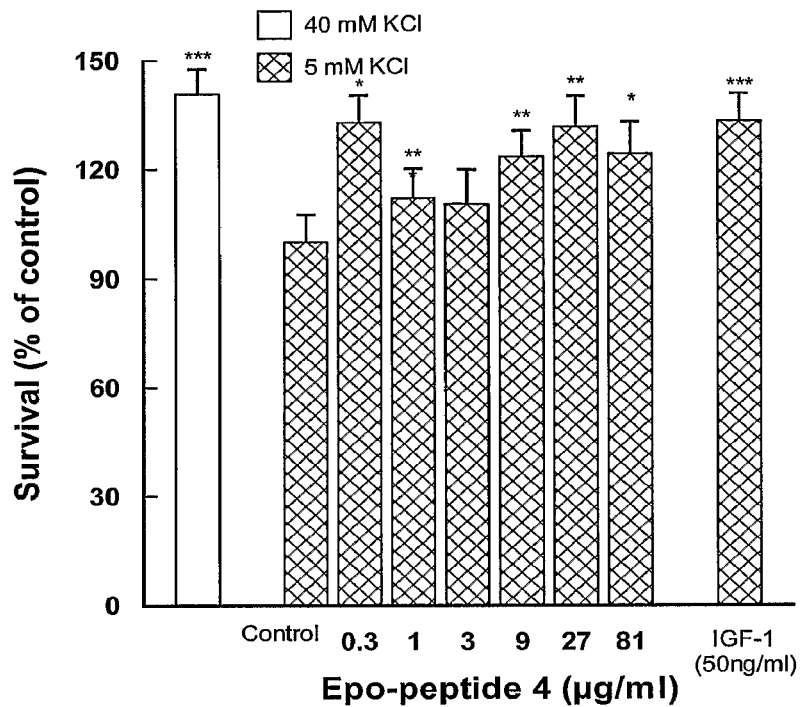

FIG. 10 Effect of Epo4 (Epo-peptide 4) (SEQ ID NO: 4) on survival of CGN in vitro.

Figure 11:
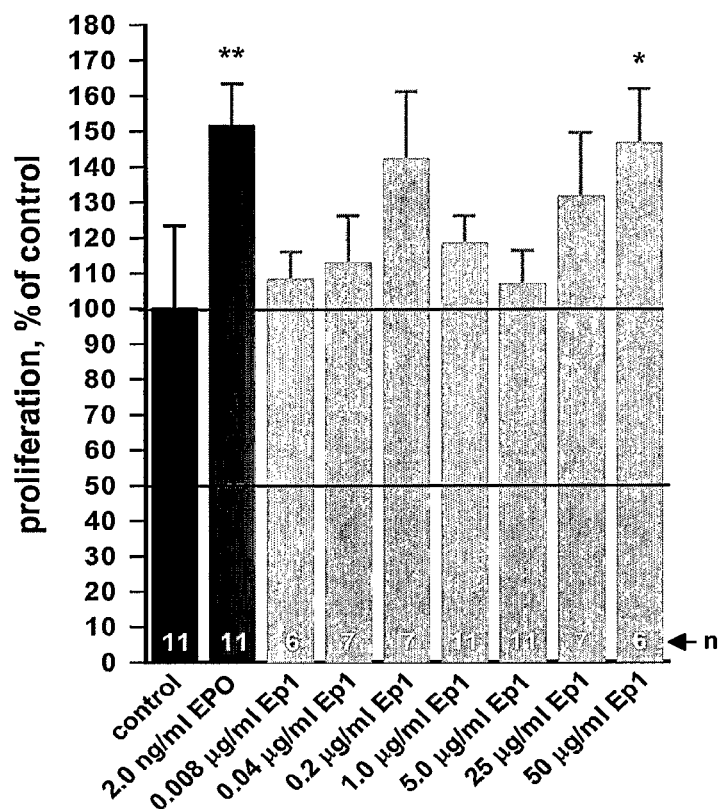

FIG. 11 Effect of Epo1 (Ep1) (SEQ ID NO: 1) on proliferation of human erythroleukemia cells TF-1 in vitro. Statistical significance was calculated in comparison with control.

Figure 12:
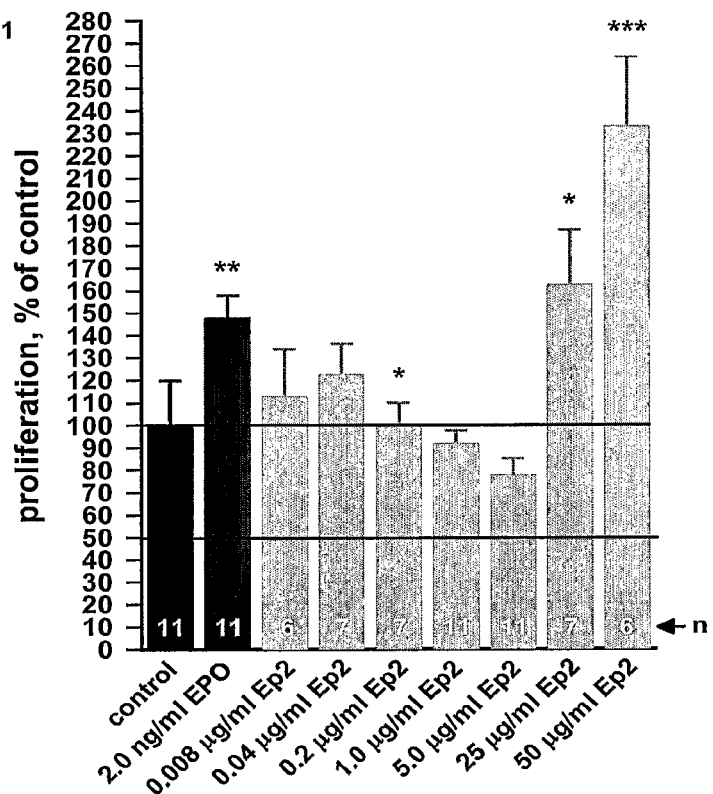

FIG. 12 Effect of Epo2 (Ep2) (SEQ ID NO: 2) on proliferation of human erythroleukemia cells TF-1 in vitro. Statistical significance was calculated in comparison with control.

Figure 13:
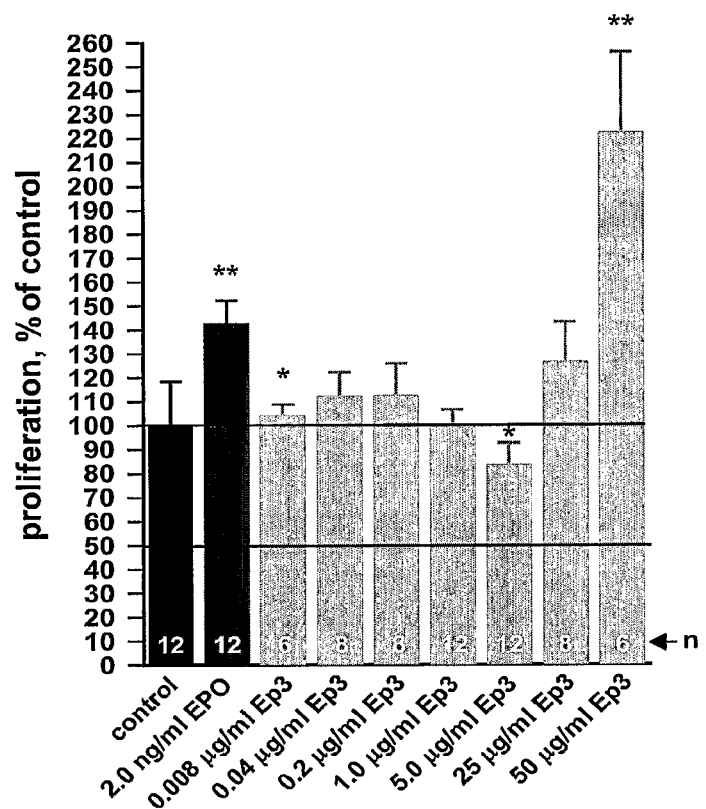

FIG. 13 Effect of Epo3 (Ep3) (SEQ ID NO:3) on proliferation of human erythroleukemia cells TF-1 in vitro. Statistical significance was calculated in comparison with control.

Figure 14:
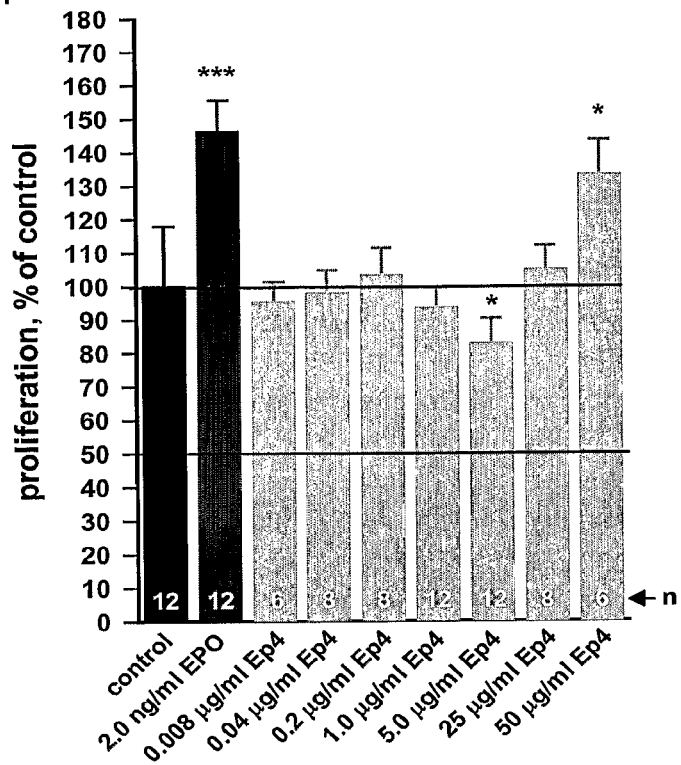

FIG. 14 Effect of Epo4 (Ep4) (SEQ ID NO: 4) on proliferation of human erythroleukemia cells TF-1. Statistical significance was calculated in comparison with control.

Figure 15:
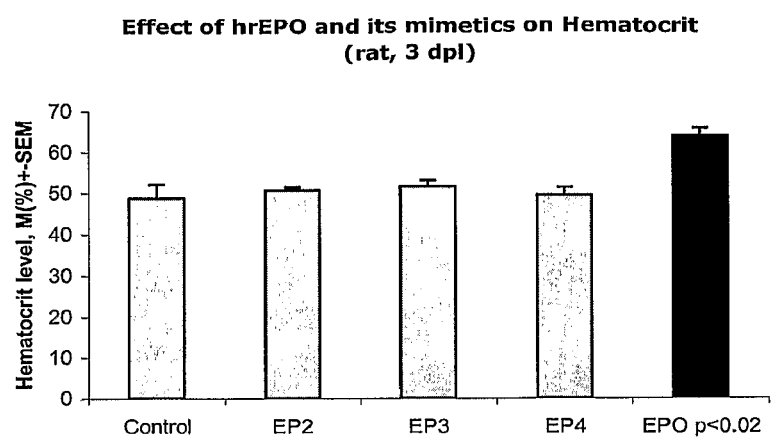

FIG. 15 Effect of recombinant human erythropoietin (EPO) and EPO mimetic peptides Epo2, Epo3 and Epo 4 (EP2, EP3 and EP4) (SEQ ID NO: 2, 3 and 4) on the hematocrit in rat brain after the brain lesion. The hematocrit (%) is significantly increased after treatment of the rats with EPO (63.7+−1.9 EPO vs 48.7+−3.35 control, p<0.02). The peptide mimetics have no statistically significant effect on the hematocrit (Ep2, Ep3, Ep4 vs control p>0.02). Control—treatment with water.

Figure 16:
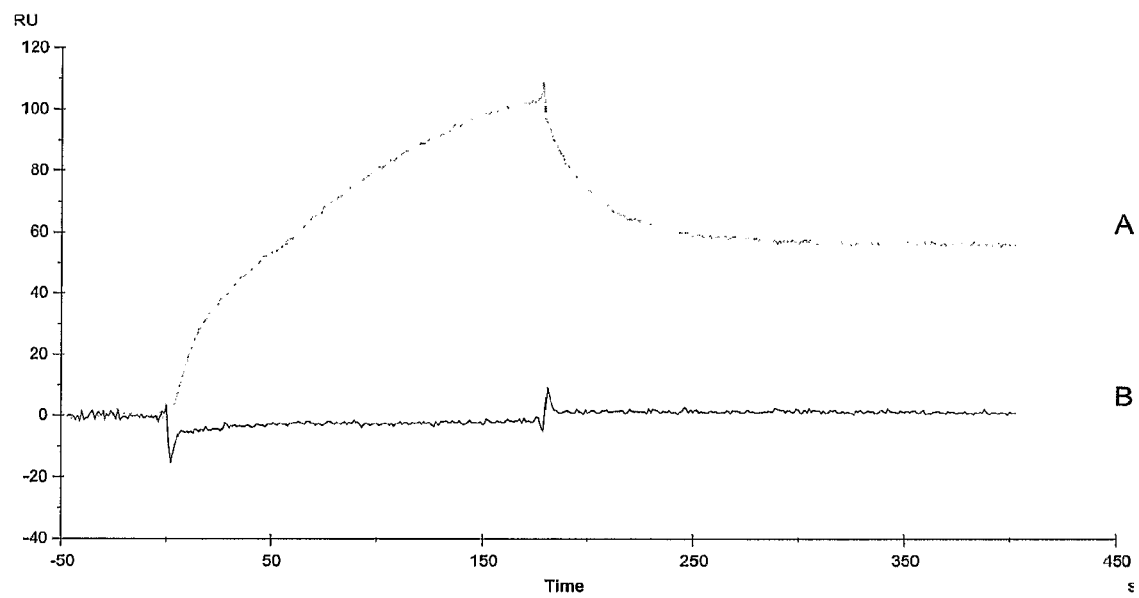

FIG. 16 Binding of recombinant erythropoietin receptor (EPOR) to the immobilized Epo3 peptide (SEQ ID NO:3). The binding was studied by SPR analysis. Three independent experiments were performed. The results show that EPOR binds to Epo3 with relatively middle association rate ($k_a$=2.1*10$^4$+−1.4*10$^4$) and slow dissociation rate ($k_d$=4.33*10$^{-5}$+−1.62*10$^{-5}$). The EPOR binds with Epo3 with overall binding affinity 4.48 nM.

A—binding of soluble EPOR to Epo3 ionic bound to the chip

B—binding of soluble EPOR to Epo3 covalently bound to the chip.

DETAILED DESCRIPTION OF THE INVENTION

Molecules with the potential to promote neurite outgrowth as well as stimulate survival, regeneration of neuronal cells, such as certain endogenous trophic factors, are prime targets in the search for compounds that facilitate for example neuronal regeneration and other forms of neuronal plasticity. Short peptide sequences of 6-25 amino acid residues have proved to be good candidate compounds useful as in research as in medical applications.

Peptide Sequences

Thus, in one aspect the invention relates to a compound, which comprises, essentially comprises or consists of at least one isolated peptide sequence comprising the amino acid sequence motif of the formula $$x^1-x^2-x^3-x^4-x^5-x^6, \quad \text{(SEQ ID NO: 43)}$$

wherein $x^1$ is a charged amino acid residue, $x^6$ is a hydrophobic amino acid residue or A, and $x^2$, $x^3$, $x^4$ and $x^5$ is any amino acid residue Beyond the presence of two most important amino acid residues in the structural motif of the invention, which are a charged residue in position 1 ($x^1$) of the motif, preferably the negatively charged residue, and a hydrophobic amino acid residues in position 6 ($x^6$), preferably L, V or Y, the invention further favours the sequences wherein the motif further comprises i) the S residue in position 2 ($x^2$) and/or ii) a hydrophobic residue in position 2 ($x^2$) and/or hydrophobic residue in position 3 ($x^3$) of the motif. Examples of such preferred motifs may be the sequences (i) R—S-$x^3$-$x^4$-$x^5$-L (SEQ ID NO:44), and (ii) R-V-$x^3$-$x^4$-$x^5$-A (SEQ ID NO:45), R-V-L-$x^4$-$x^5$-Y (SEQ ID NO:46), K-A-V-$x^4$-$x^5$-L (SEQ ID NO:47), R-$x^2$-L-$x^4$-$x^5$-L (SEQ ID NO:48), or R-S-L-$x^4$-$x^5$-L (SEQ ID NO:49). Yet, the residue S or T is in some cases preferred in position 4 ($x^4$) independently of the presence of a hydrophobic residue in position $x^2$ and/or $x^3$.

In the present application the standard one-letter code for amino acid residues as well as the standard three-letter code are applied. Abbreviations for amino acids are in accordance with the recommendations in the IUPAC-IUB joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and forms.

Where nothing is specified it is to be understood that the C-terminal amino acid of a peptide of the invention exists as the free carboxylic acid, this may also be specified as "—OH". However, the C-terminal amino acid of a compound of the invention may be the amidated derivative, which is indicated as "—NH$_2$". Where nothing else is stated the N-terminal amino acid of a polypeptide comprise a free amino-group, this may also be specified as "H-".

Where nothing else is specified amino acid can be selected from any amino acid, whether naturally occurring or not, such as alfa amino acids, beta amino acids, and/or gamma amino acids. Accordingly, the croup comprises but are not limited to: Ala, Val, Leu, Ile, Pro, Phe, Trp, Met, Gly, Ser, Thr, Cys, Tyr, Asn, Gln, Asp, Glu, Lys, Arg, His Aib, Nal, Sar, Orn, Lysine analogues, DAP, DAPA and 4Hyp.

Also, according to the invention modifications of the compounds/peptides may be performed, such as for example glycosylation and/or acetylation of the amino acids.

Basic amino acid residues are according to invention represented by the residues of amino acids Arg, Lys, and His, acidic amino acid residues—by the residues of amino acids Glu and Asp. Basic and amino acid residues constitute a group of charged amino acid residues. The group of hydrophobic amino acid residues is represented by the residues of amino acids Leu, Ile, Val, Phe, Trp, Tyr, and Met.

In one embodiment variants may be understood as exhibiting amino acid sequences gradually differing from the preferred predetermined sequence, as the number and scope of insertions, deletions and substitutions including conservative substitutions increase. This difference is measured as a reduction in homology between the predetermined sequence and the variant.

The invention relates to naturally occurring, synthetically/recombinant prepared peptide sequence/fragments, and/or peptide sequence/fragments prepared by means of enzymatic/chemical cleavage of a bigger polypeptide, wherein said peptide sequence/fragments are integral parts of the polypeptide chain, said sequences being the existing separated/isolated individual chemical units/compounds.

The present invention identifies herein a group of short individual peptide fragments which comprise the amino acid sequence motif of above and correlates the presence of the motif in the sequence with the capability of said sequence to i) induce neurite outgrowth, and/or ii) stimulate survival of neural cells, and/or stimulate synaptic plasticity, and/or iv) stimulate learning, and/or v) stimulate memory and vi) stimulate cell proliferation. This group of peptide fragments consists of the following sequences:

```
                              (SEQ ID NO: 1)
DSRVLERYLLEAKE (SEQ ID NO: 2)
NENITVPDTKVNFYAWKR (SEQ ID NO: 3)
QLHVDKAVSGLRSLTTLLRA (SEQ ID NO: 4)
RVYSNFLRGKLKLYTGEA (SEQ ID NO: 5)
DLRVLSKLLRDSHV (SEQ ID NO: 6)
PSTQPWEHVNAIQEARR (SEQ ID NO: 7)
CSRSIWLARKIRSD (SEQ ID NO: 8)
SERIDKQIRYILDGIS (SEQ ID NO: 9)
SCNMIDEIITHLKQ (SEQ ID NO: 10)
SSCLMDRHDFGFPQEEFDGNQ (SEQ ID NO: 11)
MSYNLLGFLQRSSNFQCQKLLWQLN (SEQ ID NO: 12)
CYCQDPYVKEAENLKKYFNA (SEQ ID NO: 13)
PTPVLLPAVDFSLGEWKTQM (SEQ ID NO: 14)
NETVEVISE (SEQ ID NO: 15)
NKNINLDSADGMPVASTD (SEQ ID NO: 16)
AENNLNLPKMAEKD (SEQ ID NO: 17)
ENNLRRPNLEAFNRAVKS (SEQ ID NO: 18)
QQIFNLFTTKDSSAAWDE (SEQ ID NO: 19)
DRMNFDIPEEIKQLQQFQK (SEQ ID NO: 20)
ADNGTLFLGILKNWKEESDR (SEQ ID NO: 21)
TAHKDPNAIFLSFQHLLRGKVRFL (SEQ ID NO: 22)
QTRLELYKQGLRGSLTKLKGPLTM (SEQ ID NO: 23)
LLQVAAFAYQIEELMILLEYK (SEQ ID NO: 24)
EEQARAVQMSTKVLIQ (SEQ ID NO: 25)
HIKDGDWNEFRRKLTFYLKT (SEQ ID NO: 26)
LMNADSILAVKKYFRRITLY (SEQ ID NO: 27)
KLEKEDFTRGKLMSSLHLKR (SEQ ID NO: 28)
NSNKKKRDDFEKLTNYSVTD (SEQ ID NO: 29)
PNRTSGLLETNFTAS (SEQ ID NO: 30)
KDFLLVIPFDCWEPVQE (SEQ ID NO: 31)
ELSQWTVRSIHDLRFISS (SEQ ID NO: 32)
RSFKEFLQSSLR (SEQ ID NO: 33)
FINRLTGYLRN
```

ELSPAAKTGKR (SEQ ID NO: 34)

SLIIGFAAGALYWKKRQPSL (SEQ ID NO: 35)

DELINIIDGVLRDDDKNND (SEQ ID NO: 36)

RNRVTNNVKDVTKLV (SEQ ID NO: 37)

DKLVNIVDDLVECVKE (SEQ ID NO: 38)

GLDKNTVHDQEHIMEHLEGV (SERQ ID NO: 39)

SETSDCVVSSTLSPEKDSRV (SEQ ID NO: 40)

QLHYFKMHDYDGNNLL. (SEQ ID NO: 41)

The identified above peptides according to the application may used for different applications, for example for production of different antibodies or production of different medicaments. Therefore in different embodiments the peptide sequence may be preferably selected.

Thus, in one preferred embodiment, the peptide fragment may be preferably selected from the group consisting of the peptide sequences

DSRVLERYLLEAKE (SEQ ID NO: 1)

NENITVPDTKVNFYAWKR (SEQ ID NO: 2)

QLHVDKAVSGLRSLTTLLRA (SEQ ID NO: 3)

RVYSNFLRGKLKLYTGEA. (SEQ ID NO: 4)

The above group of sequences is designated herein as Group 1. The sequences of Group 1 are derived from human erythropoietin (Swissprot Ass. No. P01588).

In another preferred embodiment, the peptide fragment may be selected from the group consisting of the peptide sequences

DLRVLSKLLRDSHV (SEQ ID NO: 5)

PTPVLLPAVDFSLGEWKTQM (SEQ ID NO: 13)

TAHKDPNAIFLSFQHLLRGKVRFL (SEQ ID NO: 21)

PNRTSGLLETNFTAS. (SEQ ID NO: 29)

The above group of sequences is designated herein as Group 2. The sequences of Group 2 are derived from human thrombopoietin (Swissprot Ass. No. P40225).

In still another preferred embodiment, the peptide fragment may be selected from the group consisting of peptide sequences

PSTQPWEHVNAIQEARR (SEQ ID NO: 6)

NETVEVISE (SEQ ID NO: 14)

QTRLELYKQGLRGSLTKLKGPLTM (SEQ ID NO: 22)

KDFLLVIPFDCWEPVQE. (SEQ ID NO: 30)

The above group of sequences is designated herein as Group 3. The sequences of Group 3 are derived from human granulocyte-macrophage colony-stimulating factor (GM-CSF, Swissprot Ass. No. P04141).

In yet another preferred embodiment, the peptide fragment may be selected from for the group consisting of the peptide sequences

CSRSIWLARKIRSD (SEQ ID NO: 7)

NKNINLDSADGMPVASTD (SEQ ID NO: 15)

LLQVAAFAYQIEELMILLEYK (SEQ ID NO: 23)

ELSQWTVRSIHDLRFISS. (SEQ ID NO: 31)

The above group of sequences is designated herein as Group 4. The sequences of Group 4 are derived from human ciliary neurotrophic factor (CNFT, Swissprot Ass. No. P26441).

In still yet another preferred embodiment, the peptide fragment may be selected from the group consisting of the peptide sequences

SERIDKQIRYILDGIS (SEQ ID NO: 8)

AENNLNLPKMAEKD (SEQ ID NO: 16)

EEQARAVQMSTKVLIQ (SEQ ID NO: 24)

RSFKEFLQSSLR. (SEQ ID NO: 32)

The above group of sequences is designated herein as Group 5. The sequences of Group 5 are derived from human interleukin-6 Swissprot Ass. No. P05231).

In other preferred embodiments the sequence may be selected either from the sequences of the group of
i) peptide sequences derived from human interleukin-3 (IL-3, Swissprot Ass. No. P08700) (Group 6):

SCNMIDEIITHLKQ (SEQ ID NO: 9)

ENNLRRPNLEAFNRAVKS (SEQ ID NO: 17)
or

HIKDGDWNEFRRKLTFYLKT; (SEQ ID NO: 25)
or ii) peptide sequences derived from human interferon alpha-1 (Swissprot Ass. No. P05231) (Group 7):

```
                                        (SEQ ID NO: 10)
SSCLMDRHDFGFPQEEFDGNQ (SEQ ID NO: 18)
QQIFNLFTTKDSSAAWDE (SEQ ID NO: 26)
LMNADSILAVKKYFRRITLY;
or
``` iii) peptide sequences derived from human interferon beta (Swissprot Ass. No P01574) (Group 8):

```
                                        (SEQ ID NO: 11)
MSYNLLGFLQRSSNFQCQKLLWQLN (SEQ ID NO: 19)
DRMNFDIPEEIKQLQQFQK (SEQ ID NO: 27)
KLEKEDFTRGKLMSSLHLKR (SEQ ID NO: 33)
FINRLTGYLRN;
or
``` iv) peptide sequences derived from human interferon gamma (Swissprot Ass. No. P05231) (Group 9):

```
                                        (SEQ ID NO: 12)
CYCQDPYVKEAENLKKYFNA (SEQ ID NO: 20)
ADNGTLFLGILKNWKEESDR (SEQ ID NO: 28)
NSNKKKRDDFEKLTNYSVTD (SEQ ID NO: 34)
ELSPAAKTGKR;
or
``` v) peptide sequences derived from human cell stem factor (Swissprot Ass. No. P21583) (Group 10):

```
                                        (SEQ ID NO: 37)
RNRVTNNVKDVTKLV (SEQ ID NO: 38)
DKLVNIVDDLVECVKE (SEQ ID NO: 40)
SETSDCVVSSTLSPEKDSRV (SEQ ID NO: 35)
SLIIGFAAGALYWKKRQPSL;
or
``` vi) peptide sequences derived from human multiple coagulation factor deficiency protein 2 (neural stem cell derived neuronal survival protein/MCD2 (Swissprot Ass. No. P21583Q8NI22) (Group 11):

```
                                        (SEQ ID NO: 39)
GLDKNTVHDQEHIMEHLEGV (SEQ ID NO: 41)
QLHYFKMHDYDGNNLL (SEQ ID NO: 36)
DELINIIDGVLRDDDKNND.
```

However, any amino acid sequence other then the above mentioned sequences, which contains the motif of the invention and is capable of at least one biological activity selected from stimulating neuronal differentiation, stimulating neurite outgrowth, stimulating survival of neural cells, enhancing synaptic plasticity, stimulating learning and memory is in the scope of protection of the invention.

Compounds, which comprise or consist of variants of the above sequences, are also in the scope of the invention.

"Variant of a peptide sequence" means that the peptides may be modified, for 5, example by substitution of one or more of the amino acid residues. Both L-amino acids and D-amino acids may be used. Other modification may comprise derivatives such as esters, sugars, etc. Examples are methyl and acetyl esters.

Variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Leu, and Ile, and independently thereof, variants, or fragments thereof, wherein at least one valine (Val) of said variant, or fragments thereof is substituted with an amino acid selected from the group of amino acids consisting of Gly. Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at east one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one asparagine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Ser, Thr, and Tyr.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:
P, A, G (neutral, weakly hydrophobic),
S, T (neutral, hydrophilic)
Q, N (hydrophilic, acid amine)
E, D (hydrophilic, acidic)
H, K, R (hydrophilic, basic)
A, L, I, V, M, F, Y, W (hydrophobic, aromatic)
C (cross-link forming)

Conservative substitutions may be introduced in any position of a preferred predetermined peptide of the invention or fragment thereof. It may however also be desirable to introduce non-conservative substitutions, particularly, but not limited to, a non-conservative substitution in any one or more positions.

A non-conservative substitution leading to the formation of a functionally equivalent fragment of the peptide of the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

The addition or deletion of an amino acid may be an addition or deletion of from 2 to to 6 amino acids, such as from 2 to 4 amino acids. However, additions of more than 6 amino acids, such as additions from 2 to 10 amino acids, are also comprised within the present invention, in the multimeric forms additions/deletions may be made individually in each monomer of the multimer.

As mentioned above, a compound of the invention may comprise, essentially comprise or consist of at least one peptide sequence containing the motif of the invention. Accordingly, a peptide sequence of the compound may have different length.

Thus, an isolated individual peptide sequence of the compound may consist of 6 or more amino acid residues. The essential amino acid motif of the invention consists of 6 amino acid residues therefore the minimal length of a peptide sequence is 6 amino acid residues. The upper limit for the number of amino acid residues in an isolated contiguous peptide sequence of the compound may vary from 7 to 50 and some cases may extend beyond 50 amino acid residues to 100 amino acid residues. However, sequences of 25-35 amino acid residues in length or less, such as 20-25, 15-20, or 10-15 amino acid residues, are within preferred embodiments of the invention. Peptide sequences comprising the motif of the invention and having the length from 7 to 15 amino acid residues are referred herein as the sequences essentially comprising the motif of the invention.

Thus, the invention preferably features compounds consisting of or comprising at least one contiguous peptide sequence of 6-25 amino acid residues. Thus in one embodiment, a peptide sequence may be from 10 to 25, such as for example from 14 to 25, in another embodiment a sequence may have the length from 14 to 20, for example from 14 to 18 amino acid residues. In some embodiments, the peptide sequence of the invention may comprise more then 25 amino acid residues, such as from 26 to 50 amino acid residues, for example 28-30, 31-35, 36-40, 41-45 or 46-49 amino acid residues, and in some cases the sequence may extends beyond 50 amino acid residues, for example such as a sequence having the length of 51-55, 56-60, 61-65, 66-71 or 72-75 amino acid residues, or 75-85 amino acid residues.

A compound of the invention may comprise more then one of the above peptide sequences. Thus, the sequences of above may be formulated as monomers, which mean that they may be represented by a single copy of an individual peptide sequence. A compound may also comprise more then one copy of the same sequence. Thus, the invention also relates to polymers of individual peptide sequences of the above. A polymer of a peptide sequence may be formulated as a contiguous peptide chain wherein an individual peptide sequence is repeated/copied two or more times, or it may a molecule, wherein the copies of an individual peptide sequence are connected to each other then the peptide bond, for example via any kind of linker grouping. An example of such polymers may be dendromeric polymers wherein the individual copies of a peptide sequence are attached to a core molecule, such as for example a lysine residue. Another example of a polymer may be the LPA (Ligand Presenting Assembly) type polymer. Polymerisation such as repetitive sequences or attachment to various carriers are well-known in the art. e.g. lysine backbones, such as lysine dendrimers carrying 4 peptides, 8 peptides, 16 peptides, or 32 peptides. Other carriers may be protein moieties, such as bovine serum albumin (BSA), or lipophilic dendrimers, or micelle-like carriers formed by lipophilic derivatives, or starburst (star-like) carbon chain polymer conjugates, or ligand presenting assembly (LPA) based on derivatives of diethylaminomethane.

A compound of the invention may comprise or consists of two or more individual peptide fragments having different amino acid sequences presented as isolated peptide sequence.

Proteins and Peptide Fragments Thereof

According to the invention an isolated peptide sequence which comprises, essentially comprises or consists of the motif described above is one embodiment derived from human erythropoietin (EPO). The invention relates to human erythropoietin having the sequence identified in the Swissprot database under ID No. P01588. In another embodiment the peptide sequence is derived from a variant or a homologue of human erythropoietin.

Thus, the invention relates to proteins, sequences of which have homology to the sequence of erythropoietin (Swissprot Ass. No. P01588). The invention defines a protein as being a homologue of human erythropoietin when the amino acid of said protein shares at least 35% homology with the sequence of erythropoietin (Swissprot Ass. No. P01588). The homology of one amino acid sequence with another amino acid sequence is defined as a percentage of identical amino acids in the two collated sequences. The homology between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90.

Preferably the invention relates to human erythropoietin structural homologues selected from

| | |
|---|---|
| thrombopoietin (Swissprot Ass. No. P40225), | 82% homology to erythropoitin, |
| granulocyte-macrophage colony-stimulating factor (GM-CSF, Swissprot Ass. No. P04141) | 63% homology to erythropoitin, |
| ciliary neurotrophic factor (CNFT, Swissprot Ass. No. P26441) | 41% of homology to erythropoitin, |
| interleukin-6 (IL-6, Swissprot Ass. No. P05231) | 45% homology to erythropoitin, |
| interleukin-3 (IL-3, Swissprot Ass. No. P08700) | 36% homology to erythropoitin, |
| interferon alpha-1 (Swissprot Ass. No. P05231) | 57% homology to erythropoitin, |
| interferon beta (Swissprot Ass. No. P01574) | 59% homology to erythropoitin, |
| interferon gamma (Swissprot Ass. No. P05231) | 41% homology to erythropoitin, |
| cell stem factor (Swissprot Ass. No. P21583) | 37% homology to erythropoitin, |
| multiple coagulation factor deficiency protein 2 (MCD2, Swissprot Ass. No. Q8NI22) | 38% homology to erythropoitin. |

According to the invention the above proteins are both structured and functional homologues of human erythropoietin.

An amino acid sequence, which is 35-100%, preferably 45-100%, more preferably 50-100%, such as about 55, 60, 65, 70, 75, 80% homologous to the sequence of erythropoietin of Swissprot Ass. No. P01588, and possesses at least one biological activity of said erythropoietin is regarded by the application as a functional homologue of erythropoietin. Nonlimited examples of functional homologues of human erythropoietin are given above. Examples of the biological activities of human erythropoietin relevant for the present application include, but not limited by stimulation of proliferation, differentiation and survival of haemopoietic cells, stimulating neuronal cell differentiation and survival. In a preferred embodiment the application relates to biological activities, which are most relevant for neural coils, such as the capability of stimulating neuronal differentiation, for example stimulating neurite outgrowth, stimulating neuronal survival, such as inhibiting apoptosis of neural cells, and/or enhancing synaptic plasticity, learning and memory. These biological functions of erythropoietin are according to the invention to be executed by an area(s) of the protein, which essentially comprise a sequence(s)

DSRVLERYLLEAKE (SEQ ID NO: 1)

NENITVPDTKVNFYAWKR (SEQ ID NO: 2)

QLHVDKAVSGLRSLTTLLRA (SEQ ID NO: 3)

RVYSNFLRGKLKLYTGEA. (SEQ ID NO: 4)

The invention also contemplates variants of human erythropoietin having the sequence of Swissprot Ass. No. P01588 as functional homologues of the protein "Variant" in the present content means i) erythropoietin-like polypeptides of non-human origin, such as other species origin, ii) recombinant molecules of human erythropoietin; iii) molecules of i) and which comprise amino acid substitutions or modifications of amino acids in relation to the sequence of Ass. No. P01588, iv) polypeptides that share 90-99% homology with the sequence of Ass. No. P01588, v) fragments of the sequence of Ass. No. P01588, which are of 90-99% of the sequence length, or vi) natural or recombinant human erythropoietin molecules which have post-translational modifications, such as for example additional/alternative glycosylation of the polypeptide chain when compared to naturally occurring erythropoietin polypeptides.

The sequences derived from human erythropoietin identified as SEQ ID NOS: 1-4 all 1) comprise the motif of the invention $$x^1\text{-}x^2\text{-}x^3\text{-}x^4\text{-}x^5\text{-}x^6, \quad \text{(SEQ ID NO: 43)}$$

wherein
$x^1$ is a charged amino acid residue,
$x^6$ is a hydrophobic amino acid residue or A,
$x^2$, $x^3$, $x^4$ and $x^5$ is any amino acid residue, and
2) possess neuritogenic activity,
3) possess survival promoting activity,
4) possess synaptic plasticity enhancing activity, and/or
5) possess learning and memory enhancing activity, and
6) possess cell proliferation stimulating activity The invention considers the presence of the motif of the invention in a peptide sequence to be essential structural element to enable the peptide sequence to induce neuronal differentiation, such as stimulate neurite growth, promote survival of neuronal cells and/or enhance synaptic plasticity, learning capability and improve memory. Accordingly, any peptide sequence of at least 6 amino acids comprising the above motif, having about 40-99% structural homology to SEQ ID NO: 1, 2, 3 or 4 and having at least one activity of the SEQ ID NO: 1, 2, 3 or 4 is considered to be a functional homologue of SEQ ID NOS: 1, 2, 3 and 4, Homology between two peptide sequences is defined as described above.

As described above, the invention preferably relates to short contiguous peptide sequences of 6 to 25 amino acids long comprising the motif of above. The invention further prefers those of the latter peptide sequences that have at least 40% homology to any of identified above fragments of EPO (SEQ ID NO; 1, 2, 3 or 4). More preferred the sequences having about 50-55, 55-60 or 60-65% homology. Yet, more preferred the sequences which are more then 65% homologous to any of the EPO peptide fragments identified herein as SEQ ID NOs: 1-4 Homology between sequences is identified as described above. However, in some embodiments a sequence which has homology to a particular sequence selected from SEQ ID NOS: 1, 2, 3 or 4, may be preferred. The invention discloses herein that the sequences of SEQ ID NOS: 1-4 vary in their activity in relation to stimulating of neurite outgrowth, neural cell survival and cell proliferation, therefore, depending on the purpose it may be favourable to select a particular sequence to achieve the maximal effect of the sequence on neurite outgrowth, cell survival or cell proliferation.

Thus, in one embodiment of the invention, such preferred sequence may be the sequence of SEQ ID NO: 1 or a sequence homologous to SEQ ID NO: 1, which may be selected form the group consisting of the sequences

```
                                    (SEQ ID NO: 5)
DLRVLSKLLRDSHV (SEQ ID NO: 6)
PSTQPWEHVNAIQEARR (SEQ ID NO: 7)
CSRSIWLARKIRSD (SEQ ID NO: 8)
SERIDKQIRYILDGIS (SEQ ID NO: 9)
SCNMIDEIITHLKQ (SEQ ID NO: 10)
SSCLMDRHDFGFPQEEFDGNQ (SEQ ID NO: 11)
MSYNLLGFLQRSSNFQCQKLLWQLN (SEQ ID NO: 12)
CYCQDPYVKEAENLKKYFNA (SEQ ID NO: 37)
RNRVTNNVKDVTKLV (SEQ ID NO: 39)
GLDKNTVHDQEHIMEHLEGV
```

The sequences homologous to SEQ ID NO: 2 may preferably be selected form the group consisting of the sequences:

```
                                    (SEQ ID NO: 3)
QLHVDKAVSGLRSLTTLLRA (SEQ ID NO: 4)
RVYSNFLRGKLKLYTGEA.

(SEQ ID NO: 5)
DLRVLSKLLRDSHV (SEQ ID NO: 13)
PTPVLLPAVDFSLGEWKTQM (SEQ ID NO: 14)
NETVEVISE (SEQ ID NO: 15)
NKNINLDSADGMPVASTD (SEQ ID NO: 16)
AENNLNLPKMAEKD (SEQ ID NO: 17)
ENNLRRPNLEAFNRAVKS (SEQ ID NO: 18)
QQIFNLFTTKDSSAAWDE (SEQ ID NO: 19)
DRMNFDIPEEIKQLQQFQK
```

```
                                    (SEQ ID NO: 20)
ADNGTLFLGILKNWKEESDR.
```

The sequences homologous to SEQ ID NO: 3 may preferably be selected form the group consisting of the sequences:

```
                                    (SEQ ID NO: 21)
TAHKDPNAIFLSFQHLLRGKVRFL (SEQ ID NO: 22)
QTRLELYKQGLRGSLTKLKGPLTM (SEQ ID NO: 23)
LLQVAAFAYQIEELMILLEYK (SEQ ID NO: 24)
EEQARAVQMSTKVLIQ (SEQ ID NO: 25)
HIKDGDWNEFRRKLTFYLKT (SEQ ID NO: 26)
LMNADSILAVKKYFRRITLY (SEQ ID NO: 27)
KLEKEDFTRGKLMSSLHLKR (SEQ ID NO: 28)
NSNKKKRDDFEKLTNYSVTD (SEQ ID NO: 40)
SETSDCVVSSTLSPEKDSRV (SEQ ID NO: 41)
QLHYFKMHDYDGNNLL.
```

A sequence homologous to SEQ ID NO: 4 may preferably be selected form the group consisting of the sequences:

```
                                    (SEQ ID NO: 29)
PNRTSGLLETNFTAS (SEQ ID NO: 30)
KDFLLVIPFDCWEPVQE (SEQ ID NO: 31)
ELSQWTVRSIHDLRFISS (SEQ ID NO: 32)
RSFKEFLQSSLR (SEQ ID NO: 33)
FINRLTGYLRN (SEQ ID NO: 34)
ELSPAAKTGKR (SEQ ID NO: 35)
SLIIGFAAGALYWKKRQPSL (SEQ ID NO: 36)
DELINIIDGVLRDDDKNND
```

The sequences of SEQ ID NOs: 5-41 are derived from the amino acid sequences of the following human EPO homologues
thrombopoietin (Swissprot Ass. No. P40225),
granulocyte-macrophage colony-stimulating factor (GM-CSF, Swissprot Ass. No. 04141),
neurotrophic factor (CNFT, Swissprot Ass. No. P20441),
interleukin-6 (IL-6, Swissprot Ass. No. P05231),
interleukin-3 (IL-3, Swissprot Ass. No. P08700),
interferon alpha-1 (Swissprot Ass. No. P05231),
interferon beta (Swissprot Ass. No. P01574),
interferon gamma (Swissprot Ass. No. P05231).
cell stem factor (Swissprot Ass. No. P21583)

multiple coagulation factor deficiency protein 2 (MCD2, Swissprot Ass. No. Q8NI22)

The term "derived" in relation to an individual peptide sequence means that said peptide sequence is originally an integral part/fragment of a naturally occurring polypeptide/protein which has been prepared as an isolated individual chemical entity by means of biochemical or chemical methods, for example by enzymatic cleavage of the original polypeptide or synthetic preparation of the peptide sequence. The present patent application relates to peptide sequences derived from the above identified proteins as isolated individual peptide fragments of sold proteins, and does not relate to the original proteins/polypeptides sequences of which include these fragments.

Individual peptide sequences/fragments of the invention possess biological activity(s) that can mimic certain biological activity(s) of the original polypeptide. Thus, the individual peptide sequence/fragment of the invention may be used as a functional equivalent/homologue of the predetermined polypeptide selected from the above identified, or a functional equivalent of human EPO or a biological fragment thereof.

Production of Individual Peptide Sequences

The peptide sequences of the present invention may be prepared by any conventional synthetic methods, recombinant DNA technologies, enzymatic cleavage of full-length proteins which the peptide sequences are derived from, or a combination of said methods.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 nd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2 nd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a fun-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell Biol. 1:854-864), the MT-1 (metallothionein gene) promoter (Palmiter et al., 1983. Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al. eds., Plenum Press, New York), or the TPI1 (U.S. Pat. No. 4,599,311) or ADH2-4c (Russell et al., 1983. Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op. cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G, A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteines. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

By SAPS peptides may be synthesised either batchwise in a polyethylene vessel equipped with a polypropylene filter for filtration or in the continuous-flow version of the polyamide solid-phase method (Dryland, A, and Sheppard, R. C., (1986) J. Chem. Soc. Perkin Trans. I, 125-137.) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality.

When synthesised, individual peptide sequences may then be formulated as multimers using well-known in the art techniques, for examples dimers of the sequences may be obtained by the LPA method described in WO 00/18791, dendrimeric polymers by the MAP synthesis described in PCT/US90/02039.

Antibody

It is an objective of the present invention to provide an antibody, antigen binding fragment or recombinant protein thereof capable of recognizing and selectively binding to an epitope on human erythropoietin, thrombopoietin, granulocyte-macrophage colony-stimulating factor (GM-CSF), ciliary neurotrophic factor (CNFT), interleukin-6 (IL-6), interleukin-3 (IL-3), interferon alpha-1, interferon beta, interferon gamma, cell stem factor, multiple coagulation factor deficiency protein 2 (MCD2), said epitope comprising at least one of the sequences selected from SEQ ID NOs:1-41, or a fragment of said sequence.

By the term "epitope" is meant the specific group of atoms (on an antigen molecule) that is recognized by (that antigen's) antibodies (thereby causing an immune response). The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA, 82(14):4592-6, 1985).

Depending on the amino acid sequences of the constant domain of their heavy chains, immunoglobulins can be assigned to different classes. There are at least five (5) major classes of immunoglobulins IgA, IgD, IgE, IgG and several of these may be further divided into subclasses (isotypes), e.g. IgG-1. IgG-3 and IgA-1 and IgA-2. The heavy chains constant domains that correspond to the different classes of immunoglobulins are called alpha ($\alpha$), delta ($\delta$), epsilon ($\epsilon$), gamma ($\gamma$) and mu ($\mu$), respectively. The light chains of antibodies can be assigned to one of two clearly distinct types, called kappa ($\kappa$) and lambda ($\lambda$), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely a adopting a $\beta$-sheet configuration, connected by three CDRs, which form loops connecting, and in some cases forming part of, the $\beta$-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, on antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and FY fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-41, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction.

(4) F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or halt of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad Sci. USA 90: 6444-6448 (1993).

The invention contemplate both polyclonal and monoclonal antibody, antigen binding fragments and recombinant proteins thereof which are capable of binding an epitope according to the invention.

The preparation of polyclonal antibodies is well-known to those skilled in the art. See, for example, Green et al. 1992. Production of Polyclonal Antisera, in: immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1938), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991. Nature 352: 624-628, as well as In Marks et al., 1991, J Mol Biol 222; 58'1-597. Another method involves humanizing a monoclonal antibody by recombinant means to generate antibodies containing human specific and recognizable sequences. See, for review. Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore. In contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in E. coli of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988. Science 242; 423-426; U.S. Pat. No. 4,946,778; and Pack, et al., 1993, BioTechnology 11; 1271-77.

Another form of an antibody fragment is a peptide coding for a single complementarity-determining region (CDR), CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example. Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab' h or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising the epitope(s) described herein, is one of the preferred embodiments of the invention.

In some instances. Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988. Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard methods in the art for producing polyclonal and monoclonal antibodies using natural or recombinant fragments of human human erythropoietin, thrombopoietin, granulocyte-macrophage colony-stimulating factor (GM-CSF), ciliary neurotrophic factor (CNFT), interleukin-6 (IL-6), interleukin-3 (IL-3), interferon alpha-1, interferon beta, interferon gamma, cell stem factor, multiple coagulation factor deficiency protein 2 (MCD2) comprising a sequence selected from any of the sequences identified as SEQ ID NO: 1-41 as an antigen. Such antibodies may be also generated using variants or fragments of peptide fragments of SEQ ID NOs: 1-41, said fragments being immunogenic fragments which meet at least two of the following criteria:
(i) being a contiguous amino acid sequence of at least 6 amino acids;
(ii) comprising an amino acid sequence derived from the sequence of human human erythropoietin, thrombopoietin, granulocyte-macrophage colony-stimulating factor (GM-CSF), ciliary neurotrophic factor (CNFT), interleukin-6 (IL-6), interleukin-3 (IL-3), interferon alpha-1, interferon beta, interferon gamma, cell stem factor or multiple coagulation factor deficiency protein 2 (MCD2).

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to an antibody, which is capable of modulating such as enhancing or attenuating, biological function of human erythropoietin, thrombopoietin, granulocyte-macrophage colony-stimulating factor (GM-CSF), ciliary neurotrophic factor (CNFT), interleukin-6 (IL-6), interleukin-3 (IL-3), interferon alpha-1, interferon beta, interferon gamma, cell stem factor or multiple coagulation factor deficiency protein 2 (MCD2), in particular a function related to neural cell growth, differentiation, survival and/or plasticity, and to an antibody, which can recognise and specifically bind the latter proteins without modulating biological activity thereof.

The invention relates to use of the above antibodies for 1) therapeutic applications when the modulation of activity of human erythropoietin, thrombopoietin, granulocyte-macrophage colony-stimulating factor (GM-CSF), ciliary neurotrophic factor (CNFT), interleukin-6 (IL-6), interleukin-3 (IL-3), interferon alpha-1, interferon beta, interferon gamma, cell stem factor or multiple coagulation factor deficiency protein 2 (MCD2) is needed, 2) detecting and/or monitoring the latter proteins in vitro and/or in vivo for diagnostic purposes, 3) research purposes, Pharmaceutical Composition The invention also relates to a pharmaceutical composition comprising one or more of the compounds defined above, wherein the compound is capable of stimulating neurite outgrowth and/or neural cell differentiation, survival of neural cells and/or stimulating learning and/or memory. Thus, the invention concerns a pharmaceutical composition capable of stimulating differentiation of neuronal cells and/or stimulating regeneration of neuronal cells, and/or stimulating neuronal plasticity in connection with learning and memory, and/or stimulating survival of neural cells.

In the present context the term "pharmaceutical composition" is used synonymously with the term "medicament".

In a composition the peptide sequences may be formulated as comprising isolated individual peptide fragments or multimers or dimers thereof as discussed above.

The pharmaceutical composition may have the described above effects on cells in vitro or in vivo, wherein the composition is administered to a subject.

The medicament of the invention comprises an effective amount of one or more of the compounds as defined above, or a composition as defined above in combination with the pharmaceutically acceptable additives. Such medicament may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration. e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 5000 µg per kilo body weight. Using monomeric forms of the compounds, the suitable dosages are often in the range of from 0.1 µg to 5000 µg per kilo body weight, such as in the range of from about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For some indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In many instances, it will be necessary to administrate the formulation multiple times. Administration may be a continuous infusion, such as intraventricular infusion or administration in more doses such as more times a day, daily, more times a week, weekly, etc. it is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, stimulating regeneration, plasticity and survival of neural cells in vitro or in vivo, said treatment involving administering an effective amount of one or more compounds as defined above.

Another strategy for administration is to implant or inject cells capable of expressing and secreting the compound in question. Thereby the compound may be produced at the location where it is going to act.

Treatment

In a further aspect, the present invention relates to said peptides, fragments, or variants thereof for use in the induction of differentiation and/or stimulation of regeneration, plasticity and/or survival of neural cells. The use is for the treatment for preventing diseases and conditions of the central and peripheral nervous system, and of the muscles or of various organs.

Treatment by the use of the compounds/compositions according to the invention is in one embodiment useful for inducing differentiation, modulating proliferation, stimulate regeneration, neuronal plasticity and survival of cells being implanted or transplanted. This is particularly useful when using compounds having a long term effect.

Thus, the treatment comprises treatment and/or prophylaxis of cell death in relation to diseases or conditions of the central and peripheral nervous system, such as postoperative nerve damage, traumatic nerve damage, e.g. resulting from spinal cord injury, impaired myelination of nerve fibers, postischaemic damage, e.g. resulting from a stroke, multiinfarct dementia, multiple sclerosis, nerve degeneration associated with diabetes mellitus, neuro-muscular degeneration, schizophrenia. Alzheimer's disease, Parkinson's disease, or Huntington's disease.

Also, in relation to diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity and survival, i.e. stimulating survival.

In yet a further embodiment the use of the compound and/or pharmaceutical composition is for the stimulation of the ability to learn and/or of the short and/or long term memory.

In particular the compound and/or pharmaceutical composition of the invention may be used in the treatment of clinical conditions, such as psychoses, such as senile and presenile organic psychotic conditions, alcoholic psychoses, drug psychoses, transient organic psychotic conditions. Alzheimer's disease, cerebral lipidoses, epilepsy, general paresis [syphilis], hepatolenticular degeneration, Huntington's chorea, Jakob-Creutzfeldt disease, multiple sclerosis. Pick's disease of the brain, syphilis, Schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders, mental retardation, disease in the nerve system and sense organs, cognitive anomalies, inflammatory disease of the central nervous system, such as meningitis, encephalitis, Cerebral degenerations such as Alzheimer's disease, Pick's disease, senile degeneration of brain, communicating hydrocephalus obstructive hydrocephalus, Parkinson's disease including other extra pyramidal disease and abnormal movement disorders, spinocerebellar disease, cerebellar ataxia, Marie's, Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, Syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis; peripheral autonomic neuropathy in disorders classified elsewhere, amyloidosis, diseases of the peripheral nerve system, brachial plexus lesions, cervical rib syndrome, costoclavicular syndrome, scalenus anterior syndrome, thoracic outlet syndrome, brachial neuritis or radiculitis, including in newborn, Inflammatory and toxic neuropathy, including acute infective polyneuritis, Guillain-Barre syndrome, Postinfectious polyneuritis, polyneuropathy in collagen vascular disease, disorders affecting multiple structures of eye, purulent endophthalmitis, diseases of the our and mastoid process, abnormality of organs and soft tissues in newborn, including in the nerve system, complications of the administration of anesthetic or other sedation in labor and delivery, diseases in the skin including infection, insufficient circulation problem, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chasm, injury to optic pathways, injury to visual cortex, unspecified blindness, injury to other cranial nerve(s), injury to other and unspecified nerves. Poisoning by drugs, medicinal and biological substances, genetic or traumatic atrophic muscle disorders; or for the treatment of diseases or conditions of various organs, such as degenerative conditions of the gonads, of the pancreas, such as diabetes mellitus type I and II, of the kidney, such as nephrosis.

A further aspect of the invention is a process of producing a pharmaceutical composition, comprising mixing an effective amount of one or more of the compounds of the invention, or a pharmaceutical composition according to the invention with one or more pharmaceutically acceptable additives or carriers, and administer an effective amount of at least one of said compound, or said pharmaceutical composition to a subject.

In one embodiment of the process as mentioned above, the compounds are used in combination with a prosthetic device, wherein the device is a prosthetic nerve guide, Thus, in a further aspect, the present invention relates to a prosthetic nerve guide, characterised in that it comprises one or more of the compounds or the pharmaceutical composition as defined above. Nerve guides are known in the art.

Another aspect of the invention relates to the use of a compound as defined above. In particular the use of a compound according to the invention is for the production of a pharmaceutical composition. The pharmaceutical composition is preferably for the treatment or prophylaxis of any of the diseases and conditions mentioned above.

In yet a further aspect the invention relates to a method of treating a disease or condition as discussed above by administering a compound as defined herein.

EXAMPLES

Example 1

Stimulation of Neurite Outgrowth in vitro

Methods:

Cerebellar granule neuron (CGN) cultures were obtained from 3-4-day-old Wistar rats (Charles River, Sulzfeld, Germany, or Moellegaard, Denmark) as previously described by Schousboe et al. (1989). Briefly, the cerebella were dissected, cleared of meninges and blood vessels, chopped, and trypsinized. The neurons were washed in the presence of DNAse 1 and soybean trypsin inhibitor (Sigma), and cellular debris was pelleted by centrifugation; the cells resuspended and then plated on poly-L-lysine (PLL; Sigma)-coated or uncoated microtiter plates in Neurobasal medium supplemented with 4% (w/v) bovine serum albumin (BSA), 2% (v/v) B27, 1% (v/v) glutamax, 100 U/ml penicillin, 100 gi/ml streptomycin, 4.5 g D-glucose/L (Sigma) 0.25% (v/v) sodium pyruvate, and 2% (v/v) 1 M HEPES (Gibco BRL).

Results and Conclusions

Three out of four Epo fragments (SEQ ID NO: 2, 3, and 4) strongly induce neurite outgrowth from CGN in a dose dependent manner, whereas the recombinant Epo protein (rhEPO) and the peptide having the sequence SEQ ID NO: 1 do net have any neuritogenic activity. The effect of 24 h treatment of CGN cultures with the peptides and rhEPO is demonstrated in FIGS. 1-5.

Example 2

Stimulation of Survival of Neural Cells in vitro

Methods:

Primary cultures of CGN were plated at a density of 100 000 cells/$cm^2$ on poly-L-lysine coated 8-well permanox slides in Neurobasal-A medium (Gibco BRL) supplemented with 2% (v/v) B27, 0.5% (v/v) glutamax, 100 units/mL penicillin, 100 µg/mL streptomycin and KCl, making the final concentration of KCl in the medium 40 mm, Twenty-four hours after plating, Ara-C (Sigma-Aldrich) was added to a final concentration of 10 µm to avoid proliferation of glial cells, after which the neurons were allowed to differentiate for a further 6 days at 37° C. Apoptotic cell death was induced by washing twice and changing the medium to Basal Medium Eagle (BME; Gibco BRL) supplemented with 1% (v/v) glutamine, 100 U/mL, penicillin and 100 µg/mL streptomycin, 3.5 g d-glucose/L and 1% (v/v) sodium pyruvate (Gibco BRL) together with various concentrations of peptide. Thereby the concentration of potassium in the cultures was reduced to 5 mm KCl (D'Mello et al. 1993). Two days after induction of apoptosis, the cells were fixed with 4% (v/v) formaldehyde and stained with Hoechst 33258 as described for the survival assay employing hippocampal neurons.

Results and Conclusions:

All Epo-derived peptides and the recombinant Epo protein are capable of protection of CGN induced to undergo apoptosis. The effect is dose-dependent. The Epo-derived peptides 2, 3 and 4 (SEQ ID NOs: 2-4) have the strongest neuroprotective effect, which is comparable to the effect of insulin growth factor-1 (IGF-1), a known strong promoter of cell survival The effect of the treatment of CGN cultures with the peptides is demonstrated in FIGS. 6-10.

Example 3

Stimulation of proliferation of haemopoietic cells

Methods:

Evaluation of the effect of four EPO-derived peptides on cell proliferation was performed using a TF-1 cell line. The TF-1 cell line was established from sample from patient with severe pancytopenia (human erythroleukemia). The growth of these cells is dependent of the presence of the granulocyte-macrophage colony-stimulating factor (GM-SCF). The TF-1 cells were grown in Dulbecco's Modified Eagle Medium (DMEM) supplemented with 10% (v/v) heat inactivated foetal calf serum (FCS), 2 mM GlutaMAX, penicillin (100 U/ml) and streptomycin (100 µg/ml), 10 mM HEPES, 1 mM sodium pyruvate, 1% fungizone. The growth medium was supplemented with 2 ng/ml GM-CSF. Cell proliferation was determined using a Biotrak ELISA system, version 2 (Amersham Biosciences, UK). The procedure is based on measurement of the levels of 5-bromo-2'-deoxyuridine (BrdU) incorporation during DNA synthesis in proliferating cells. Briefly, passaged cells were washed once with starving medium (culturing medium without GM-CSF) then plated in 96-well Nuclon culture microplates (Nuno, Denmark) at a density of 5000 cells/well and grown in starving medium containing 0.008, 0.04, 0.2, 1.0, 5.0, 25 and 50 µg/ml of the tested compounds. As a positive control the human recombinant erythropoietin (EPO) (Calbiochem, Denmark) was used in a concentration of 2.0 ng/ml. TF-1 cells were allowed to grow in the presence of peptides for 24 h and than to all wells (except negative controls) BrdU was added to a final concentration of 10 µM and cultures were further incubated for 24 h, fixed and processed according to the procedure recommended by manufacturer, Results/conclusions:

The recombinant Epo protein in a concentration of 2 ng/ml stimulates proliferation of TF-1 cells. The Epo-derived peptides, Epo3 and Epo4, (SEQ ID NOs:3 and 4) stimulate proliferation of TF-1 cells in a concentration of 50 µg/ml, but not in concentration 25 µg/ml or below. The Epo-derived peptide 2, Epo2, (SEQ ID NO:2) stimulates proliferation of TF-1 cells in concentrations of 25 and 50 µg/ml, but not in concentration below 25 µg/ml. The Epo-derived peptide 1. Epo1, stimulates proliferation of TF-1 cells in a concentration of 50 µg/ml and probably had a stimulatory effect in a concentration of 0.2 µg/ml.

General conclusion

All four tested Epo peptides Epo1, 2, 3 and 4 (SEQ ID NOs:1-4) possess biological activity. However, biological activity of Epo fragments and the full-length recombinant Epo protein is different. Thus, peptides Epo2, 3 and 4 are capable of stimulating neurite outgrowth, whereas the full-length recombinant Epo protein does not possess neurite stimulatory activity, nor does the Epo1 peptide. However, all peptides and the Epo protein as well are potent in stimulating neuronal cells, survival. All peptides and the Epo protein are also capable of stimulating haemopoietic cell proliferation, most potent among them being the Epo peptides 3 and 4. Interestingly, biological activity of different Epo peptides depends on their concentration in cell medium. Thus, the neuritogenic activity of both Epo peptides 2, 3 and 4 is higher when the peptides are present in low concentrations, whereas stimulation of cell proliferation demands the presence of significantly larger amounts of the peptides.

Example 4

Therapeutic Effects of Erythropoietin Mimetic Peptides Epo 2, 3 and 4 in Rat Brain in Vivo Experimental Setup:

Male rats (wistar) (tree groups, 5 rats/group) were injected s.c with different Epo peptides (each group individually with Epo 2, Epo 3 or Epo 4) three times according to the scheme:
1. the day before the lesion: a single injection of a peptide per animal (1 mg/100 g animal weight);
2. the $1^{st}$ day after the lesion: a single injection of a peptide per animal (1 mg/100 g animal weight):
3. the $2^{nd}$ day after the lesion: a single injection of a peptide per animal (1 mg/100 g animal weight);
4. the $3^{rd}$ day after the lesion: animals are sacrificed.

Control groups were a group (4 rats) injected with the vehicle (water) and a group (4 rats), injected with human recombinant EPO (hrEPO) in dose 50 µg/100 g rat according to the above scheme.

Methods

1. Traumatic Brain Injury

A traumatic brain injury (TBI) was induced by applying dry ice (−78 C) to the extracranial surface of the skull for 60 sec, which induces a focal injury in the right fronto-parietal cortex. Three days after the lesion (3 dpl) rats were deeply anesthetized with Brietal (10 mg/100 gr) and fixed by transcardial perfusion with 0.9% NaCl and 0.3% heparin, followed by Zamboni's fixative. The brains were removed, dehydrated according to the standard protocol, embedded in paraffin, and cut in 6-µm-thick frontal sections for further evaluation by immunohistochemistry and TUNEL.

2. Immunocytochemistry

For immunohistochemistry the sections of the brains were incubated overnight with polyclonal rabbit anti-cow GFAP, GAP-43, 8-oxoguanine, or PSA-NCAM antibodies 1:250 (Dakopatts). The primary antibodies were detected in the sections with biotinylated secondary antibodies followed by incubation with streptavidin-biotin-peroxidase (30 min). Afterwards, the sections were incubated with biotinylated tyramide and streptavidin-peroxidase complex (NEN, Life Science Products, USA, code NEL700A) prepared following the manufacturer recommendations, and visualized with 0.015% $H_2O_2$ in DAB/TBS for 10 min.

3. TUNEL (In Situ Detection of DNA Fragmentation):

Terminal deoxynucleotidyl transferase (TdT)-mediated biotin-linked deoxynucleotide nick end labeling (TUNE-1) was performed using the Fragment End Labeling (FragEL™) Detection Kit (Calbiochem, USA, code QIA33). The FragEL kit contains all the materials used below and each step was performed according to the manufacturer recommendations. The tissue was processed and rehydrated as mentioned above, and sections were incubated with 20 µg/ml (proteinase K for 20 min to strip off nuclear proteins. After immersion in equilibration buffer for 20 min, sections were incubated with TdT and biotin-labeled deoxynucleotides (dNTP-biotin) in a humified chamber at 37° C. for 1.5 hr. This was followed by washing with the buffer and stop solution for 5 min at room temperature to stop the reaction. After washing in TBS and incubation in blocking buffer for 10 min, the sections were incubated with Peroxidase-Streptavidin for 30 min and afterwards, DAB was used as chromogen. The sections were counterstained with methyl-green.

Results:

1. The EPO mimetics clearly increase astrocytosis in the rat brain after TBI as judged by GFAP IHC. The mast pronounced increase in reactive astrogliosis is obtained after treating the rats with the Epo 2 peptide; and then with the Epo 3 peptide. The Epo 4 peptide has the least effect. Treatment with the EPO protein results in slightly increased astrocytosis in comparison to control rats (treated with water), which does increases astrocytosis very slightly, if any.

2. The Epo peptides inhibit programmed cell death in the areas surrounding the necrotic cavity after TBI. All groups show TUNEL-positive apoptotic cells after TBI, but the numbers of dying cells is the highest in control group (treated with water) compared to the rats receiving the EPO protein and Epo 2 peptide. The lowest level of apoptosis is observed in Epo 3 and Epo 4 treated groups of rats.

3. Immunostaining with a marker of oxidative DNA damage, 8-oxoguanine, demonstrates a higher number of the 8-oxoguanine positive cells in the control group. The EPO and Epo 4 treated rats have a significantly reduced oxidative DNA damage relative to control, and the lowest number of the 8-oxoguanine positive cells is observed in Epo 2 and Epo 3 treated rats.

4 EPO mimetic peptides stimulate neuroplasticity and neurite outgrowth in vivo after TBI of rat brain as judged by PSA-NCAM and GAP-43 immunostaining of rat brain tissue sections. The Epo 3 and Epo 4 treatment significantly increases the level of PSA-NCAM staining both in the area adjusted to the lesion, of Neural Stem Cells (NSC) and in the subventricular zone (SVZ), whereas only a few cells in the lesion area of control rats are PSA-NCAM positive, Treatment with Epo 2 and Epo 3 also stimulates neurite outgrowth in the area of cortical lesion and in the choroid plexus, hippocampus, and hypothalamus.

4. The hematocrit (%) significantly increases after EPO treatment (63.7+−1.9 EPO vs 43.7+−3.35 control, p<0.02). All peptide mimetics Epo 2, Epo 3 and Epo 4 have no significant effect on the hematocrit (Ep2, Ep3, Ep4 vs control p>0.02). The results are demonstrated in FIG. 15.

Example 5

Binding of the Epo 3 Peptide to Recombinant Erythropoietin Receptor (EPOR-Fc)

The binding of Epo 3 to EPOR-Fc was studied by SPR analysis. The Epo 3 peptide was immobilized on a chip and the chip was incubated with soluble recombinant EPOR-Fc under standard conditions. Three independent experiments were performed. The results show that EPOR binds to the immobilized Epo 3 (ionic bonded with the chip) with association rate $k_a = 2.1 \cdot 10^4 +/- 1.4 \cdot 10^4$ and dissociation rate $k_d = 4.33 \cdot 10^{-5} +/- 1.62 \cdot 10^{-5}$. The affinity of the binding of EPOR to Ep3 is 4.48 nM. Epo 3 covalently bonded to the chip does not bind to EPOR. The results of binding are shown on FIG. 16.

The invention claimed is:

1. A method for treating a condition of the central nervous system selected from Alzheimer's disease, epilepsy, and traumatic brain injury, said method comprising administering to a subject in need thereof an effective amount of (i) a peptide consisting of 10 to 20 consecutive amino acids of SEQ ID NO:3; or (ii) a peptide consisting of 10 to 20 amino acids and having more than 80% homology to 10 to 20 consecutive amino acids of SEQ ID NO:3;
wherein said peptide is capable of stimulating neurite outgrowth, and/or promoting survival of neural cells, and/or stimulating neural cell proliferation.

2. The method of claim 1, wherein said condition of the central nervous system is Alzheimer's disease.

3. The method of claim 1, wherein the subject is human.

4. The method of claim 1, wherein the peptide (i) consists of 10 to 15 consecutive amino acids of SEQ ID NO:3, or (ii) consists of 10 to 15 amino acids and has more than 80% homology to 10 to 15 consecutive amino acids of SEQ ID NO:3.

5. The method of claim 1, wherein the peptide consists of from 10 to 15 consecutive amino acids of SEQ ID NO:3.

6. The method of claim 1, wherein the peptide consists of the amino acid sequence of SEQ ID NO:3.

7. The method of claim 1, wherein the arginine amino acid residue at position 12 of SEQ ID NO:3 is arginine or conservatively substituted with a histidine or a lysine amino acid residue in the corresponding position within said peptide.

8. The method of claim 1, wherein said peptide is administered in a dosage of 0.1 µg to 500 µg per kilogram body weight.

9. A method for treating a condition of the central nervous system selected from Alzheimer's disease, epilepsy, and traumatic brain injury, said method comprising administering to a subject in need thereof an effective amount of a compound consisting of two or more linked peptides linked via one or more linker groups, each peptide either (i) consisting of 10 to 20 consecutive amino acids of SEQ ID NO:3, or (ii) consisting of 10 to 20 amino acids and having more than 80% homology to 10 to 20 consecutive amino acids of SEQ ID NO:3; wherein each peptide is capable of stimulating neurite outgrowth, and/or promoting survival of neural cells, and/or stimulating neural cell proliferation; wherein said linker groups are selected from the group consisting of peptide bonds forming a polymer of the two or more polypeptides, dendrimeric polymers, Ligand Presenting Assembly (LPA)-type polymers, lysine dendrimers, bovine serum albumin (BSA), lipophilic dendrimers, micelle-like carriers, starburst carbon chain polymer conjugates, and ligand presenting assembly polymers based on derivatives of diethylaminomethane, with the proviso that the amino acid sequence of the linked peptides is not identical to the amino acid sequence of naturally occurring erythropoietin.

10. The method of claim 9, wherein a dimer or a tetramer of said peptides is administered.

* * * * *

SEQUENCE LISTING

```
<160> NUMBER OF SEQ ID NOS: 52

<210> SEQ ID NO 1
<211> LENGTH: 14
<212> TYPE: PRT
<213> ORGANISM: Artificial sequence
<220> FEATURE:
<223> OTHER INFORMATION: Derived from human erythropoietin, Swiss Prot
      P01588

<400> SEQUENCE: 1

Asp Ser Arg Val Leu Glu Arg Tyr Leu Leu Glu Ala Lys Glu
1               5                   10

<210> SEQ ID NO 2
<211> LENGTH: 18
<212> TYPE: PRT
<213> ORGANISM: Artificial sequence
<220> FEATURE:
<223> OTHER INFORMATION: Derived from human erythropoietin, Swiss Prot
      P01588

<400> SEQUENCE: 2

Asn Glu Asn Ile Thr Val Pro Asp Thr Lys Val Asn Phe Tyr Ala Trp
1               5                   10                  15

Lys Arg
```

<210> SEQ ID NO 3
<211> LENGTH: 20
<212> TYPE: PRT
<213> ORGANISM: Artificial sequence
<220> FEATURE:
<223> OTHER INFORMATION: Derived from human erythropoietin, Swiss Prot
      P01588

<400> SEQUENCE: 3

Gln Leu His Val Asp Lys Ala Val Ser Gly Leu Arg Ser Leu Thr Thr
1               5                   10                  15

Leu Leu Arg Ala
            20

<210> SEQ ID NO 4
<211> LENGTH: 18
<212> TYPE: PRT
<213> ORGANISM: Artificial sequence
<220> FEATURE:
<223> OTHER INFORMATION: Derived from human erythropoietin, Swiss Prot
      P01588

<400> SEQUENCE: 4

Arg Val Tyr Ser Asn Phe Leu Arg Gly Lys Leu Lys Leu Tyr Thr Gly
1               5                   10                  15

Glu Ala

<210> SEQ ID NO 5
<211> LENGTH: 14
<212> TYPE: PRT
<213> ORGANISM: Artificial sequence
<220> FEATURE:
<223> OTHER INFORMATION: Derived from human thrombopoietin, Swiss Prot
      P40225.

<400> SEQUENCE: 5

Asp Leu Arg Val Leu Ser Lys Leu Leu Arg Asp Ser His Val
1               5                   10

<210> SEQ ID NO 6
<211> LENGTH: 17
<212> TYPE: PRT
<213> ORGANISM: Artificial sequence
<220> FEATURE:
<223> OTHER INFORMATION: Derived from human GM-CSF, Swiss Prot P04141

<400> SEQUENCE: 6

Pro Ser Thr Gln Pro Trp Glu His Val Asn Ala Ile Gln Glu Ala Arg
1               5                   10                  15

Arg

<210> SEQ ID NO 7
<211> LENGTH: 14
<212> TYPE: PRT
<213> ORGANISM: Artificial sequence
<220> FEATURE:
<223> OTHER INFORMATION: Derived from human CNFT, Swiss Prot P26441

<400> SEQUENCE: 7

Cys Ser Arg Ser Ile Trp Leu Ala Arg Lys Ile Arg Ser Asp
1               5                   10

<210> SEQ ID NO 8
<211> LENGTH: 16

```
<212> TYPE: PRT
<213> ORGANISM: Artificial sequence
<220> FEATURE:
<223> OTHER INFORMATION: Derived from human interleukin-6, Swiss Prot
      P05231

<400> SEQUENCE: 8

Ser Glu Arg Ile Asp Lys Gln Ile Arg Tyr Ile Leu Asp Gly Ile Ser
1               5                   10                  15

<210> SEQ ID NO 9
<211> LENGTH: 14
<212> TYPE: PRT
<213> ORGANISM: Artificial sequence
<220> FEATURE:
<223> OTHER INFORMATION: Derived from human interleukin-3, Swiss Prot
      P08700

<400> SEQUENCE: 9

Ser Cys Asn Met Ile Asp Glu Ile Ile Thr His Leu Lys Gln
1               5                   10

<210> SEQ ID NO 10
<211> LENGTH: 21
<212> TYPE: PRT
<213> ORGANISM: Artificial sequence
<220> FEATURE:
<223> OTHER INFORMATION: Derived from human interferon alpha-1, Swiss
      Prot P05231

<400> SEQUENCE: 10

Ser Ser Cys Leu Met Asp Arg His Asp Phe Gly Phe Pro Gln Glu Glu
1               5                   10                  15

Phe Asp Gly Asn Gln
            20

<210> SEQ ID NO 11
<211> LENGTH: 24
<212> TYPE: PRT
<213> ORGANISM: Artificial sequence
<220> FEATURE:
<223> OTHER INFORMATION: Derived from human interferon beta, Swiss Prot
      P01574

<400> SEQUENCE: 11

Met Ser Tyr Asn Leu Leu Gly Phe Leu Gln Arg Ser Ser Asn Phe Gln
1               5                   10                  15

Cys Gln Lys Leu Leu Trp Gln Leu
            20

<210> SEQ ID NO 12
<211> LENGTH: 20
<212> TYPE: PRT
<213> ORGANISM: Artificial sequence
<220> FEATURE:
<223> OTHER INFORMATION: Derived from human interferon gamma, Swiss Prot
      P05231

<400> SEQUENCE: 12

Cys Tyr Cys Gln Asp Pro Tyr Val Lys Glu Ala Glu Asn Leu Lys Lys
1               5                   10                  15

Tyr Phe Asn Ala
            20

<210> SEQ ID NO 13
<211> LENGTH: 20
```

```
<212> TYPE: PRT
<213> ORGANISM: Artificial sequence
<220> FEATURE:
<223> OTHER INFORMATION: Derived from human thrombopoietin, Swiss Prot
      P40225

<400> SEQUENCE: 13

Pro Thr Pro Val Leu Leu Pro Ala Val Asp Phe Ser Leu Gly Glu Trp
1               5                   10                  15

Lys Thr Gln Met
            20

<210> SEQ ID NO 14
<211> LENGTH: 9
<212> TYPE: PRT
<213> ORGANISM: Artificial sequence
<220> FEATURE:
<223> OTHER INFORMATION: Derived from human GM-CSF, Swiss Prot P04141

<400> SEQUENCE: 14

Asn Glu Thr Val Glu Val Ile Ser Glu
1               5

<210> SEQ ID NO 15
<211> LENGTH: 18
<212> TYPE: PRT
<213> ORGANISM: Artificial sequence
<220> FEATURE:
<223> OTHER INFORMATION: Derived from human CNFT, Swiss Prot P26441

<400> SEQUENCE: 15

Asn Lys Asn Ile Asn Leu Asp Ser Ala Asp Gly Met Pro Val Ala Ser
1               5                   10                  15

Thr Asp

<210> SEQ ID NO 16
<211> LENGTH: 14
<212> TYPE: PRT
<213> ORGANISM: Artificial sequence
<220> FEATURE:
<223> OTHER INFORMATION: Derived from human interleukin-6, Swiss Prot
      P05231

<400> SEQUENCE: 16

Ala Glu Asn Asn Leu Asn Leu Pro Lys Met Ala Glu Lys Asp
1               5                   10

<210> SEQ ID NO 17
<211> LENGTH: 18
<212> TYPE: PRT
<213> ORGANISM: Artificial sequence
<220> FEATURE:
<223> OTHER INFORMATION: Derived from human interleukin-3, Swiss Prot
      P08700

<400> SEQUENCE: 17

Glu Asn Asn Leu Arg Arg Pro Asn Leu Glu Ala Phe Asn Arg Ala Val
1               5                   10                  15

Lys Ser

<210> SEQ ID NO 18
<211> LENGTH: 18
<212> TYPE: PRT
<213> ORGANISM: Artificial sequence
<220> FEATURE:
<223> OTHER INFORMATION: Derived from human interferon alpha-1, Swiss
```

```
        Prot P05231

<400> SEQUENCE: 18

Gln Gln Ile Phe Asn Leu Phe Thr Thr Lys Asp Ser Ser Ala Ala Trp
1               5                   10                  15

Asp Glu

<210> SEQ ID NO 19
<211> LENGTH: 19
<212> TYPE: PRT
<213> ORGANISM: Artificial sequence
<220> FEATURE:
<223> OTHER INFORMATION: Derived from human interferon beta, Swiss Prot
      P01574

<400> SEQUENCE: 19

Asp Arg Met Asn Phe Asp Ile Pro Glu Glu Ile Lys Gln Leu Gln Gln
1               5                   10                  15

Phe Gln Lys

<210> SEQ ID NO 20
<211> LENGTH: 20
<212> TYPE: PRT
<213> ORGANISM: Artificial sequence
<220> FEATURE:
<223> OTHER INFORMATION: Derived from human interferon gamma, Swiss Prot
      P05231

<400> SEQUENCE: 20

Ala Asp Asn Gly Thr Leu Phe Leu Gly Ile Leu Lys Asn Trp Lys Glu
1               5                   10                  15

Glu Ser Asp Arg
            20

<210> SEQ ID NO 21
<211> LENGTH: 24
<212> TYPE: PRT
<213> ORGANISM: Artificial sequence
<220> FEATURE:
<223> OTHER INFORMATION: Derived from human thrombopoietin, Swiss Prot
      P40225

<400> SEQUENCE: 21

Thr Ala His Lys Asp Pro Asn Ala Ile Phe Leu Ser Phe Gln His Leu
1               5                   10                  15

Leu Arg Gly Lys Val Arg Phe Leu
            20

<210> SEQ ID NO 22
<211> LENGTH: 24
<212> TYPE: PRT
<213> ORGANISM: Artificial sequence
<220> FEATURE:
<223> OTHER INFORMATION: Derived from human GM-CSF, Swiss Prot P04141

<400> SEQUENCE: 22

Gln Thr Arg Leu Glu Leu Tyr Lys Gln Gly Leu Arg Gly Ser Leu Thr
1               5                   10                  15

Lys Leu Lys Gly Pro Leu Thr Met
            20

<210> SEQ ID NO 23
<211> LENGTH: 21
<212> TYPE: PRT
```

<213> ORGANISM: Artificial sequence
<220> FEATURE:
<223> OTHER INFORMATION: Derived from human CNFT, Swiss Prot P26441

<400> SEQUENCE: 23

Leu Leu Gln Val Ala Ala Phe Ala Tyr Gln Ile Glu Glu Leu Met Ile
1               5                   10                  15

Leu Leu Glu Tyr Lys
            20

<210> SEQ ID NO 24
<211> LENGTH: 16
<212> TYPE: PRT
<213> ORGANISM: Artificial sequence
<220> FEATURE:
<223> OTHER INFORMATION: Derived from human interleukin-6, Swiss Prot
      P05231

<400> SEQUENCE: 24

Glu Glu Gln Ala Arg Ala Val Gln Met Ser Thr Lys Val Leu Ile Gln
1               5                   10                  15

<210> SEQ ID NO 25
<211> LENGTH: 20
<212> TYPE: PRT
<213> ORGANISM: Artificial sequence
<220> FEATURE:
<223> OTHER INFORMATION: Derived from human interleukin-3, Swiss Prot
      P08700

<400> SEQUENCE: 25

His Ile Lys Asp Gly Asp Trp Asn Glu Phe Arg Arg Lys Leu Thr Phe
1               5                   10                  15

Tyr Leu Lys Thr
            20

<210> SEQ ID NO 26
<211> LENGTH: 20
<212> TYPE: PRT
<213> ORGANISM: Artificial sequence
<220> FEATURE:
<223> OTHER INFORMATION: Derived from human interferon alpha-1, Swiss
      Prot P05231

<400> SEQUENCE: 26

Leu Met Asn Ala Asp Ser Ile Leu Ala Val Lys Lys Tyr Phe Arg Arg
1               5                   10                  15

Ile Thr Leu Tyr
            20

<210> SEQ ID NO 27
<211> LENGTH: 20
<212> TYPE: PRT
<213> ORGANISM: Artificial sequence
<220> FEATURE:
<223> OTHER INFORMATION: Derived from human interferon beta, Swiss Prot
      P01574

<400> SEQUENCE: 27

Lys Leu Glu Lys Glu Asp Phe Thr Arg Gly Lys Leu Met Ser Ser Leu
1               5                   10                  15

His Leu Lys Arg
            20

<210> SEQ ID NO 28

-continued

```
<211> LENGTH: 20
<212> TYPE: PRT
<213> ORGANISM: Artificial sequence
<220> FEATURE:
<223> OTHER INFORMATION: Derived from human interferon gamma, Swiss Prot
      P05231.

<400> SEQUENCE: 28

Asn Ser Asn Lys Lys Lys Arg Asp Asp Phe Glu Lys Leu Thr Asn Tyr
1               5                   10                  15

Ser Val Thr Asp
            20

<210> SEQ ID NO 29
<211> LENGTH: 15
<212> TYPE: PRT
<213> ORGANISM: Artificial sequence
<220> FEATURE:
<223> OTHER INFORMATION: Derived from human thrombopoietin, Swiss Prot
      P40225

<400> SEQUENCE: 29

Pro Asn Arg Thr Ser Gly Leu Leu Glu Thr Asn Phe Thr Ala Ser
1               5                   10                  15

<210> SEQ ID NO 30
<211> LENGTH: 17
<212> TYPE: PRT
<213> ORGANISM: Artificial sequence
<220> FEATURE:
<223> OTHER INFORMATION: Derived from human GM-CSF, Swiss Prot P04141

<400> SEQUENCE: 30

Lys Asp Phe Leu Leu Val Ile Pro Phe Asp Cys Trp Glu Pro Val Gln
1               5                   10                  15

Glu

<210> SEQ ID NO 31
<211> LENGTH: 18
<212> TYPE: PRT
<213> ORGANISM: Artificial sequence
<220> FEATURE:
<223> OTHER INFORMATION: Derived from human CNFT, Swiss Prot P26441

<400> SEQUENCE: 31

Glu Leu Ser Gln Trp Thr Val Arg Ser Ile His Asp Leu Arg Phe Ile
1               5                   10                  15

Ser Ser

<210> SEQ ID NO 32
<211> LENGTH: 12
<212> TYPE: PRT
<213> ORGANISM: Artificial sequence
<220> FEATURE:
<223> OTHER INFORMATION: Derived from human interleukin-6, Swiss Prot
      P05231

<400> SEQUENCE: 32

Arg Ser Phe Lys Glu Phe Leu Gln Ser Ser Leu Arg
1               5                   10

<210> SEQ ID NO 33
<211> LENGTH: 11
<212> TYPE: PRT
<213> ORGANISM: Artificial sequence
<220> FEATURE:
```

<223> OTHER INFORMATION: Derived from human interferon beta, Swiss Prot
       P01574

<400> SEQUENCE: 33

Phe Ile Asn Arg Leu Thr Gly Tyr Leu Arg Asn
1               5                   10

<210> SEQ ID NO 34
<211> LENGTH: 11
<212> TYPE: PRT
<213> ORGANISM: Artificial sequence
<220> FEATURE:
<223> OTHER INFORMATION: Derived from human interferon gamma, Swiss Prot
       P05231

<400> SEQUENCE: 34

Glu Leu Ser Pro Ala Ala Lys Thr Gly Lys Arg
1               5                   10

<210> SEQ ID NO 35
<211> LENGTH: 20
<212> TYPE: PRT
<213> ORGANISM: Artificial sequence
<220> FEATURE:
<223> OTHER INFORMATION: Derived from human cell stem factor, Swiss Prot
       P21583

<400> SEQUENCE: 35

Ser Leu Ile Ile Gly Phe Ala Ala Gly Ala Leu Tyr Trp Lys Lys Arg
1               5                   10                  15

Gln Pro Ser Leu
            20

<210> SEQ ID NO 36
<211> LENGTH: 19
<212> TYPE: PRT
<213> ORGANISM: Artificial sequence
<220> FEATURE:
<223> OTHER INFORMATION: Derived from human multiple coagulation factor
       deficiency protein 2 (neural stem cell derived neuronal survival
       protein/MCD2), Swiss Prot P21583Q8NI22

<400> SEQUENCE: 36

Asp Glu Leu Ile Asn Ile Ile Asp Gly Val Leu Arg Asp Asp Asp Lys
1               5                   10                  15

Asn Asn Asp

<210> SEQ ID NO 37
<211> LENGTH: 15
<212> TYPE: PRT
<213> ORGANISM: Artificial sequence
<220> FEATURE:
<223> OTHER INFORMATION: Derived from human cell stem factor, Swiss Prot
       P21583

<400> SEQUENCE: 37

Arg Asn Arg Val Thr Asn Asn Val Lys Asp Val Thr Lys Leu Val
1               5                   10                  15

<210> SEQ ID NO 38
<211> LENGTH: 16
<212> TYPE: PRT
<213> ORGANISM: Artificial sequence
<220> FEATURE:
<223> OTHER INFORMATION: Derived from human cell stem factor, Swiss Prot
       P21583

```
<400> SEQUENCE: 38

Asp Lys Leu Val Asn Ile Val Asp Asp Leu Val Glu Cys Val Lys Glu
1               5                   10                  15

<210> SEQ ID NO 39
<211> LENGTH: 20
<212> TYPE: PRT
<213> ORGANISM: Artificial sequence
<220> FEATURE:
<223> OTHER INFORMATION: Derived from human multiple coagulation factor
      deficiency protein 2 (neural stem cell derived neuronal survival
      protein/MCD2), Swiss Prot P21583Q8NI22

<400> SEQUENCE: 39

Gly Leu Asp Lys Asn Thr Val His Asp Gln Glu His Ile Met Glu His
1               5                   10                  15

Leu Glu Gly Val
            20

<210> SEQ ID NO 40
<211> LENGTH: 20
<212> TYPE: PRT
<213> ORGANISM: Artificial sequence
<220> FEATURE:
<223> OTHER INFORMATION: Derived from human cell stem factor, Swiss Prot
      P21583

<400> SEQUENCE: 40

Ser Glu Thr Ser Asp Cys Val Val Ser Ser Thr Leu Ser Pro Glu Lys
1               5                   10                  15

Asp Ser Arg Val
            20

<210> SEQ ID NO 41
<211> LENGTH: 16
<212> TYPE: PRT
<213> ORGANISM: Artificial sequence
<220> FEATURE:
<223> OTHER INFORMATION: Derived from human multiple coagulation factor
      deficiency protein 2 (neural stem cell derived neuronal survival
      protein/MCD2), Swiss Prot P21583Q8NI22

<400> SEQUENCE: 41

Gln Leu His Tyr Phe Lys Met His Asp Tyr Asp Gly Asn Asn Leu Leu
1               5                   10                  15

<210> SEQ ID NO 42
<211> LENGTH: 193
<212> TYPE: PRT
<213> ORGANISM: Homo sapiens

<400> SEQUENCE: 42

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
```

```
                    85                  90                  95
Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 43
<211> LENGTH: 6
<212> TYPE: PRT
<213> ORGANISM: Artificial sequence
<220> FEATURE:
<223> OTHER INFORMATION: Motif sequence
<220> FEATURE:
<221> NAME/KEY: misc_feature
<222> LOCATION: (1)..(1)
<223> OTHER INFORMATION: Xaa can be any charged amino acid
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any hydrophobic amino acid or Ala

<400> SEQUENCE: 43

Xaa Xaa Xaa Xaa Xaa Xaa
1               5

<210> SEQ ID NO 44
<211> LENGTH: 6
<212> TYPE: PRT
<213> ORGANISM: Artificial sequence
<220> FEATURE:
<223> OTHER INFORMATION: Motif sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
```

```
<400> SEQUENCE: 44

Arg Ser Xaa Xaa Xaa Leu
1               5

<210> SEQ ID NO 45
<211> LENGTH: 6
<212> TYPE: PRT
<213> ORGANISM: Artificial sequence
<220> FEATURE:
<223> OTHER INFORMATION: Motif sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 45

Arg Val Xaa Xaa Xaa Ala
1               5

<210> SEQ ID NO 46
<211> LENGTH: 6
<212> TYPE: PRT
<213> ORGANISM: Artificial sequence
<220> FEATURE:
<223> OTHER INFORMATION: Motif sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 46

Arg Val Leu Xaa Xaa Tyr
1               5

<210> SEQ ID NO 47
<211> LENGTH: 6
<212> TYPE: PRT
<213> ORGANISM: Artificial sequence
<220> FEATURE:
<223> OTHER INFORMATION: Motif sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 47

Lys Ala Val Xaa Xaa Leu
1               5

<210> SEQ ID NO 48
<211> LENGTH: 6
<212> TYPE: PRT
<213> ORGANISM: Artificial sequence
<220> FEATURE:
<223> OTHER INFORMATION: Motif sequence
```

```
<220> FEATURE:
<221> NAME/KEY: misc_feature
<222> LOCATION: (2)..(2)
<223> OTHER INFORMATION: Xaa can be any na

```
<220> FEATURE:
<221> NAME/KEY: misc_feature
<222> LOCATION: (5)..(5)
<223> OTHER INFORMATION: Xaa can be any naturally occurring amino acid

<400> SEQUENCE: 51

Lys Val Xaa Xaa Xaa Ala
1               5

<210> SEQ ID NO 52
<211> LENGTH: 6
<212> TYPE: PRT
<213> ORGANISM: Artificial sequence
<220> FEATURE:
<223> OTHER INFORMATION: Motif sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 52

Lys Ala Xaa Xaa Xaa Leu
1               5
```